(12) United States Patent  (10) Patent No.: US 7,458,810 B2
Bergersen                  (45) Date of Patent:     Dec. 2, 2008

(54) DENTAL APPLIANCE HAVING AN ALTERED VERTICAL THICKNESS BETWEEN AN UPPER SHELL AND A LOWER SHELL WITH AN INTEGRATED HINGING MECHANISM TO ATTACH AN UPPER SHELL AND A LOWER SHELL AND A SYSTEM AND A METHOD FOR TREATING MALOCCLUSIONS

(76) Inventor: Earl O. Bergersen, 950 Green Bay Rd., Winnetka, IL (US) 60093

( * ) Notice: Subject to any disclaimer, the term of this patent is extended or adjusted under 35 U.S.C. 154(b) by 287 days.

(21) Appl. No.: 10/665,326

(22) Filed: Sep. 18, 2003

(65) Prior Publication Data

US 2005/0037311 A1    Feb. 17, 2005

Related U.S. Application Data

(60) Provisional application No. 60/412,507, filed on Sep. 20, 2002.

(51) Int. Cl.
  *A61C 3/00* (2006.01)
(52) U.S. Cl. ........................................ 433/6
(58) Field of Classification Search ............ 433/6, 433/80; 128/861, 862
  See application file for complete search history.

(56) References Cited

U.S. PATENT DOCUMENTS

| 3,724,075 | A | | 4/1973 | Kesling |
| 3,837,081 | A | | 9/1974 | Kesling |
| 4,073,061 | A | | 2/1978 | Bergersen |
| 4,105,032 | A | | 8/1978 | Blomstedt |
| 4,139,944 | A | | 2/1979 | Bergersen |
| 4,330,272 | A | * | 5/1982 | Bergersen ............ 433/5 |
| 4,370,129 | A | | 1/1983 | Huge |
| 4,371,336 | A | | 2/1983 | Hilleman |

(Continued)

FOREIGN PATENT DOCUMENTS

WO    PCT/US03/29667    9/2003

OTHER PUBLICATIONS

Written Opinion for PCT/US03/29667 mailed Jun. 16, 2004.

(Continued)

*Primary Examiner*—Cris L. Rodriguez
*Assistant Examiner*—Sunil K Singh
(74) *Attorney, Agent, or Firm*—Patents +TMS, P.C.

(57) ABSTRACT

A dental appliance having increased or decreased thickness between an upper shell and a lower shell in combination with a hinging mechanism and a system and a method for treating malocclusions are provided. The dental appliance may have an upper shell and a lower shell which receive upper teeth and lower teeth, respectively, of a user. The upper shell and the lower shell may be attached at a hinge. The dental appliance may have an increased thickness between the upper shell and the lower shell as well as an increased thickness of the hinge. In an embodiment, the dental appliance may have a decreased vertical thickness and an insertable hinging mechanism. The dental appliance may then extend treatment of malocclusions to the rear teeth of the user and may correct a dental condition, such as, for example, overbite, overjet, open bite, crowding, rotations, spacing, cross-bites, gummy smiles and temporomandibular joint problems.

80 Claims, 33 Drawing Sheets

U.S. PATENT DOCUMENTS

| | | | |
|---|---|---|---|
| 4,396,373 A | 8/1983 | Dellinger | |
| 4,568,280 A | 2/1986 | Ahlin | |
| 4,591,341 A | 5/1986 | Andrews | |
| 4,784,605 A | 11/1988 | Bergersen | |
| 4,799,884 A | 1/1989 | Bergersen | |
| 4,830,612 A | 5/1989 | Bergersen | |
| 4,898,535 A | 2/1990 | Bergersen | 433/6 |
| 4,919,612 A | 4/1990 | Bergersen | |
| 4,983,334 A | 1/1991 | Adell | |
| 4,986,751 A | 1/1991 | Bergersen | |
| 5,028,231 A | 7/1991 | Hall | |
| 5,037,294 A | 8/1991 | Bergersen | |
| 5,037,295 A | 8/1991 | Bergersen | |
| 5,042,506 A | 8/1991 | Liberati | |
| D323,215 S | 1/1992 | Bergersen | D24/180 |
| 5,211,559 A * | 5/1993 | Hart et al. | 433/80 |
| 5,328,362 A | 7/1994 | Watson et al. | |
| 5,334,218 A | 8/1994 | Johnson | |
| 5,338,190 A | 8/1994 | Tregillis | |
| 5,536,168 A * | 7/1996 | Bourke | 433/6 |
| 5,624,257 A * | 4/1997 | Farrell | 433/6 |
| 5,645,420 A | 7/1997 | Bergersen | |
| 5,683,244 A | 11/1997 | Truax | |
| 5,779,470 A | 7/1998 | Kussick | |
| 5,814,074 A | 9/1998 | Branam | |
| 5,816,799 A | 10/1998 | Parker | |
| 5,876,199 A | 3/1999 | Bergersen | |
| 5,882,192 A | 3/1999 | Bergersen | |
| 5,911,576 A | 6/1999 | Ulrich et al. | |
| 5,975,893 A | 11/1999 | Chishti et al. | |
| 6,129,084 A | 10/2000 | Bergersen | 128/848 |
| 6,299,440 B1 | 10/2001 | Phan et al. | |
| 6,454,565 B2 | 9/2002 | Phan et al. | |
| 6,505,625 B1 | 1/2003 | Uenishi | |

OTHER PUBLICATIONS

Search Report for PCT/US03/29667 mailed Dec. 29, 2003.
Int'l Prel. Rep. Pat, Mar. 24, 2005, Bergersen.

* cited by examiner

FIG. 18A
FIG. 18B
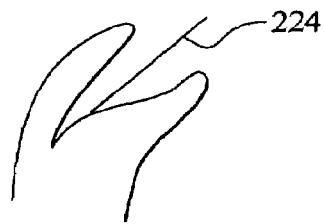
FIG. 18C
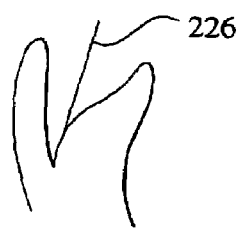
FIG. 18D
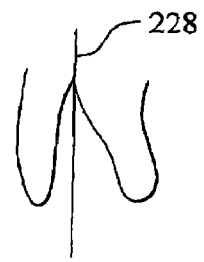
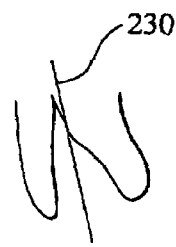
FIG. 18E

DENTAL APPLIANCE HAVING AN ALTERED VERTICAL THICKNESS BETWEEN AN UPPER SHELL AND A LOWER SHELL WITH AN INTEGRATED HINGING MECHANISM TO ATTACH AN UPPER SHELL AND A LOWER SHELL AND A SYSTEM AND A METHOD FOR TREATING MALOCCLUSIONS This application claims the benefit of U.S. Provisional Application Ser. No. 60/412,507, filed Sep. 20, 2002.

BACKGROUND OF THE INVENTION

The present invention relates to a dental appliance having increased thickness between an upper shell and a lower shell and a system and a method for treating malocclusions. More specifically, the present invention relates to a dental appliance which may have an upper shell and a lower shell which may be hingedly attached. The upper shell and the lower shell, as well as the hinge, may have an increased thickness in comparison to known dental appliances. As a result, the dental appliance may be used to treat malocclusions such as, for example, overjet or overbite. It is generally known to provide dental care to a patient. Typically, the patient visits, for example, a dentist or other type of care provider at the office of the care provider. The dentist, upon examination of the patient, may provide the patient with a dental appliance to treat the condition of the patient. For example, a patient may have an overbite which may require a dental appliance to be placed within the mouth of the patient.

The examination may determine a size or a shape of an upper shell and a lower shell of a dental appliance which may be provided to the patient. The upper shell and the lower shell receive upper teeth and lower teeth, respectively, of the patient. The upper shell and the lower shell are worn within the mouth of the patient to treat the dental condition. In some cases, the upper shell and the lower shell are connected by a hinge at an end of the dental appliance. The hinge is positioned towards a rear of the mouth of the user when the dental appliance is worn. The hinge prevents the dental appliance from slipping from the mouth of the user.

However, a number of deficiencies exist with dental appliances both when utilizing a hinge and when the upper shell and the lower shell are permanently fixed to each other. For example, a jaw of an individual opens and closes in a manner similar to a hinge. As a result, a dental appliance utilizing a hinge which fixes an upper shell and a lower shell may require a significant reduction in material at a rearward portion of the dental appliance. Specifically, a dental appliance narrows vertically near a portion which receives a first permanent molar and a second permanent molar. Material at the rearward portion of the dental appliance is often weak and may not proceed far enough rearward to completely cover the last tooth and to provide sufficient support bucco-lingually, or from an inside wall of the dental appliance to an outside wall.

To remedy the weakness of the material at the rearward portion, extra material is added to a distal portion of an isthmus of the dental appliance and/or at the hinge area; specifically, at an end of the dental appliance where the upper shell and the lower shell are fixed to the hinge, which is closest to the rear of the mouth when worn. However, the extra material often interferes with a free maximum eruption of a rearmost molar and prevents the molar from erupting and often does not cover the last molar completely. As a result, an overbite, for example, of a patient, may collapse or revert to a previous stage or may have difficulty in fully correcting in the first place.

A need, therefore, exists for a dental appliance and a system and a method for treating malocclusions wherein an upper shell and a lower shell may be sized to extend treatment of the malocclusion to the rear teeth of the user.

SUMMARY OF THE INVENTION

The present invention relates to a dental appliance having increased thickness between an upper shell and a lower shell and a system and a method for treating malocclusions. The dental appliance may have an upper shell and a lower shell which may receive upper and lower teeth, respectively, of a user. The upper shell and the lower shell may be connected in any way to enable the upper shell and the lower shell to be separate while maintaining contact. In addition, the upper shell and the lower shell may have a thickness between them which may be greater than a thickness demonstrated in known dental appliances. Moreover, the means by which the upper shell and the lower shell are connected may require an increase in a vertical thickness which may be greater than a thickness demonstrated in known dental appliances.

The increased thickness between the upper shell and the lower shell, as well as the increased thickness of the rearward portion, may enable the dental appliance to be positioned further into the mouth of the user. The dental appliance may then treat molars at a rear of the mouth of the user. In addition, the increased thickness between the upper shell and the lower shell may stimulate muscles within the mouth of the user when the user places the dental appliance within the mouth. The hinge, or other means of connecting the upper shell and the lower shell of the dental appliance, may allow the entire dental appliance to be resilient due to the increased thickness of the rear portion. As a result, the means for connecting the upper shell and the lower shell may restrict adverse lateral movement of a jaw of the user.

To this end, in an embodiment of the present invention, a dental appliance is provided which is worn in a mouth of a user having one or more types of teeth wherein one of the types of teeth is molars wherein the molars are located furthest rearward into the mouth of the user. The dental appliance has a generally U-shaped base having an occlusal surface wherein the occlusal surface contacts the teeth when the base is worn wherein the base has a thickness defined between a first end and a second end wherein the occlusal surface contacts each molar of the user when the base is worn to prevent the molar from achieving a malocclusion position.

In an embodiment, the dental appliance has a hinge connected to the base wherein the hinge enables the base to be folded.

In an embodiment, the base is translucent.

In an embodiment, the occlusal surface is flat.

In an embodiment, the dental appliance has hooks extending from the base.

In an embodiment, the dental appliance has a wire imbedded within the base.

In an embodiment, the base is constructed from a first material and a second material wherein the first material has a lesser degree of rigidity than the second material.

In another embodiment of the present invention, a dental appliance is provided which is worn in a mouth of a user having an upper arch having upper teeth and a lower arch having lower teeth and a tongue. The dental appliance has a generally U-shaped upper base which contacts upper teeth of the user when the upper base is worn. The dental appliance also has a generally U-shaped lower base adjacent to the upper base wherein the lower base contacts lower teeth of the user when the lower base is worn wherein the upper base and the lower base define an interior surface having a concave portion wherein the concave portion has a wall which prevents the tongue of the user from contacting the lower arch when the tongue is in a resting position.

In an embodiment, the dental appliance has holes within the base wherein the user breathes through the holes.

In an embodiment, the dental appliance has lingual tabs extending from the lower base wherein the lingual tabs extend rearward into the mouth.

In an embodiment, the dental appliance has one or more sockets within the upper base wherein the sockets are sized to fit at least two or more teeth of the user.

In an embodiment, the dental appliance has ribs formed within the upper base wherein the ribs guide the teeth into a correct position.

In an embodiment, the upper base is constructed from a moisture-absorbent material.

In another embodiment of the present invention, a dental appliance is provided which is worn in a mouth of a user having upper teeth and lower teeth wherein the upper teeth and the lower teeth are comprised of one or more types of teeth wherein one of the types of teeth is molars wherein the molars are located furthest rearward into the mouth of the user. The dental appliance has a generally U-shaped upper base having an upper occlusal surface wherein the upper occlusal surface contacts the upper teeth and guides the upper teeth into a correct position. The dental appliance also has a generally U-shaped lower base connected to the upper base wherein the lower base has a lower occlusal surface wherein the lower occlusal surface contacts the lower teeth and guides the lower teeth into a correct position and wherein the upper occlusal surface and the lower occlusal surface are adjacent and have a combined thickness wherein the upper occlusal surface contacts each molar of the user when the upper base and the lower base are worn to prevent the molar from achieving a malocclusion position.

In an embodiment, the dental appliance has sockets within the upper base wherein the sockets are square in shape.

In an embodiment, the upper base is marked to indicate to the user how to position the upper base within the mouth.

In an embodiment, a hinge connecting the upper base and the lower base wherein the hinge allows the upper base to be pivoted toward the lower base.

In an embodiment, the lower base is wider than the upper base.

In an embodiment, the dental appliance has a shield extending from the upper base wherein the shield contacts a front of the mouth.

In an embodiment, the dental appliance has sockets within the upper base wherein the sockets are customized to a shape of the teeth of the user.

It is, therefore, an advantage of the present invention to provide a dental appliance having increased thickness between an upper shell and a lower shell and a system and a method for treating malocclusions.

Another advantage of the present invention is to provide a dental appliance having increased thickness between an upper shell and a lower shell and a system and a method for treating malocclusions which enables eruption of rear teeth in a mouth of a user.

Still another advantage of the present invention is to provide a dental appliance having increased thickness between an upper shell and a lower shell and a system and a method for treating malocclusions which provides a means for maintaining contact between the upper shell and lower shell and further maintaining a relative position between the upper shell and the lower shell.

Yet another advantage of the present invention is to provide a dental appliance having increased thickness between an upper shell and a lower shell and a system and a method for treating malocclusions which enables alignment of an upper jaw and a lower jaw.

Moreover, an advantage of the present invention is to provide a dental appliance having increased thickness between an upper shell and a lower shell and a system and a method for treating malocclusions which enables the dental appliances to be positioned further rearward into a mouth of a user.

A further advantage of the present invention is to provide a dental appliance having increased thickness between an upper shell and a lower shell and a system and a method for treating malocclusions which prevent lateral movement of a lower jaw of a user.

A further advantage of the present invention is to provide a dental appliance having increased thickness between an upper shell and a lower shell and a system and a method for treating malocclusions which may prevent shifting of the jaws in an antero-posterior (front to back) direction and creates a stable forward position of the lower jaw in relation to the upper jaw.

A further advantage of the present invention is to provide a dental appliance having increased thickness between an upper shell and a lower shell and a system and a method for treating malocclusions which may allow preformed sockets for various sized mouths based on statistical standards of both shapes and sizes to be ideally arranged which may or may not be combined with preformed slots for two or more teeth to be placed in various areas of the mouth of a deciduous dentition, mixed dentition and/or a permanent dentition.

A further advantage of the present invention is to provide a dental appliance having increased thickness between an upper shell and a lower shell and a system and a method for treating malocclusions which may have a jaw arrangement such that a deciduous dentition is provided with an incisal overjet and/or overbite that may be about 1.5 mm to 2 mm; a mixed dentition overjet and/or overbite of about 1 to 1.5 mm; and an adult overjet and/or overbite of about 0.5 mm to 0 mm.

A further advantage of the present invention is to provide a dental appliance having increased thickness between an upper shell and a lower shell and a system and a method for treating malocclusions which may have an appliance made of a resilient transparent material.

A further advantage of the present invention is to provide a dental appliance having increased thickness between an upper shell and a lower shell and a system and a method for treating malocclusions which may have an appliance made partly of a water-absorbent material and may or may not be combined with a non-water absorbent material to determine the level of wear and/or cooperation.

A further advantage of the present invention is to provide a dental appliance having increased thickness between an upper shell and a lower shell and a system and a method for treating malocclusions which may have an appliance with more vertical thickness of material in front than in back to create depression of the front teeth and eruption of the back teeth to correct a vertical overbite.

A further advantage of the present invention is to provide a dental appliance having increased thickness between an upper shell and a lower shell and a system and a method for treating malocclusions which may have an appliance with less vertical thickness of material in front than in the back to create depression of the rear teeth and eruption of the front teeth to correct an anterior open bite.

A further advantage of the present invention is to provide a dental appliance having increased thickness between an upper shell and a lower shell and a system and a method for treating malocclusions which may have a hollowed out area on the upper lingual area of the flange to encourage the tongue to assume an elevated position to encourage a widening of the upper arch and discourage poor swallowing patterns and/or anterior tongue thrust swallowing habits.

A further advantage of the present invention is to provide a dental appliance having increased thickness between an upper shell and a lower shell and a system and a method for treating malocclusions which may have a protrusion in the lower lingual area at the midline to remind the tongue not to be thrust forward during swallowing.

A further advantage of the present invention is to provide a dental appliance having increased thickness between an upper shell and a lower shell and a system and a method for treating malocclusions which may have a slight depression or elevation in the upper lingual area of the appliance to remind the patient where to place the tongue during normal swallowing.

A further advantage of the present invention is to provide a dental appliance having increased thickness between an upper shell and a lower shell and a system and a method for treating malocclusions which may provide additional expansion of the upper posterior segment to aid in the correction of bilateral or unilateral upper lingual crossbites.

A further advantage of the present invention is to provide a dental appliance having increased thickness between an upper shell and a lower shell and a system and a method for treating malocclusions which may provide an additional expansion of the lower posterior segment to correct scissor-type bites by expansion of the lower arch.

A further advantage of the present invention is to provide a dental appliance having increased thickness between an upper shell and a lower shell and a system and a method for treating malocclusions which may have holes at the front parting line to aid in the patients who have to breathe through the mouth.

A further advantage of the present invention is to provide a dental appliance having increased thickness between an upper shell and a lower shell and a system and a method for treating malocclusions which may have extensions and thickening of the buccal and lingual margins to give added strength in bucco-lingual movement of the posterior teeth.

A further advantage of the present invention is to provide a dental appliance having increased thickness between an upper shell and a lower shell and a system and a method for treating malocclusions which may provide lower lingual tabs extending down (inferiorly) on either side of the midline to keep the mandible in an advanced position to correct overjet, and/or extending laterally to improve movement of lower lateral incisors forwards from a lingual position labially into the arch.

A further advantage of the present invention is to provide a dental appliance having increased thickness between an upper shell and a lower shell and a system and a method for treating malocclusions which may have an antero-posterior adjustment of the arches (front to back) by moving the lower jaw back several millimeters (1 to 5 mm) to correct Class III type (lower jaw protrusions) jaw relations.

A further advantage of the present invention is to provide a dental appliance having increased thickness between an upper shell and a lower shell and a system and a method for treating malocclusions which may have different angulations to the upper and/or lower front teeth for various corrections relating to the tipping or inclination (torqueing) of the front teeth of various type malocclusions.

A further advantage of the present invention is to provide a dental appliance having increased thickness between an upper shell and a lower shell and a system and a method for treating malocclusions which may have appliances for the extraction of two upper premolars, two lower premolars, and four premolars in various sizes for different sized teeth.

A further advantage of the present invention is to provide a dental appliance having increased thickness between an upper shell and a lower shell and a system and a method for treating malocclusions which may have appliances in different sizes with only three lower incisors present.

A further advantage of the present invention is to provide a dental appliance having increased thickness between an upper shell and a lower shell and a system and a method for treating malocclusions which may have appliances with further rearward extensions to fully cover and even slightly more than fully cover the second deciduous molars in deciduous dentition appliances; the first permanent molars in mixed dentition appliances; and the second permanent molars in adult dentition appliances; as well as two upper premolar extraction appliances, two lower premolar extraction as well as four premolar extraction appliances as well as Class III, expansion appliances and all those mentioned above.

A further advantage of the present invention is to provide a dental appliance having increased thickness between an upper shell and a lower shell and a system and a method for treating malocclusions which may have an upward extension to the upper labial margin to more securely keep the appliance from slipping backward when the mouth opens and/or better correction of overjet; and/or to better control aberrant eruptions of the upper and/or lower anterior teeth when the extension is added to the lower labial margin.

A further advantage of the present invention is to provide a dental appliance having increased thickness between an upper shell and a lower shell and a system and a method for treating malocclusions which may have an appliance with clasps to better retain the appliance to the upper and/or lower teeth.

A further advantage of the present invention is to provide a dental appliance having increased thickness between an upper shell and a lower shell and a system and a method for treating malocclusions which may have hooks and/or tubes to insert other appliances into a preformed appliance, such as a head gear, bumper, elastics, or the like.

A further advantage of the present invention is to provide a dental appliance having increased thickness between an upper shell and a lower shell and a system and a method for treating malocclusions which may have no individual sockets but only a single slot to guide and straighten the teeth in one or more various sizes.

A further advantage of the present invention is to provide a dental appliance having increased thickness between an upper shell and a lower shell and a system and a method for treating malocclusions which may have a flattened occlusal surface to the posterior teeth to compensate for various occlusal surface anatomy to prevent cuspal and occlusal surface interferences.

A further advantage of the present invention is to provide a dental appliance having increased thickness between an upper shell and a lower shell and a system and a method for treating malocclusions which may have almost complete elimination of the lingual posterior shield in combination with a widened posterior area of the teeth with or without angled slots to the distal at the buccal side to allow the posterior teeth to be pushed buccally and/or distally by the tongue pressing on the teeth from the lingual.

A further advantage of the present invention is to provide a dental appliance having increased thickness between an upper shell and a lower shell and a system and a method for treating malocclusions which may be molded in an open position to have the plastic or other material set in an open position and/or to have the appliance molded with a sheet of metal to provide the slit opening and prior to cooling the appliance can cool and set the hinged area in an open position and/or slit or cut and have the hinged area reheated and let cool in an open position.

A further advantage of the present invention is to provide a dental appliance having increased thickness between an upper shell and a lower shell and a system and a method for treating malocclusions which may have larger sockets and a larger arch to encourage expansion and spaces to be created for the correction of crowding.

A further advantage of the present invention is to provide a dental appliance having increased thickness between an upper shell and a lower shell and a system and a method for treating malocclusions which may provide a method of molding a fluoride compound such as stannous or sodium fluoride into the plastic or other material as the appliance is molded.

A further advantage of the present invention is to provide a dental appliance having increased thickness between an upper shell and a lower shell and a system and a method for treating malocclusions which may provide a method of loading the appliance(s) with a fluoride compound to soak the fluoride liquid into the interior of the appliance and when worn by the patient, the fluoride leaches out to gradually impregnate the teeth. Alternatively, a gel may be placed into the appliance at the time the appliance is worn by the patient.

A further advantage of the present invention is to provide a dental appliance having increased thickness between an upper shell and a lower shell and a system and a method for treating malocclusions which may provide a method of loading a bleaching gel into the appliance when the appliance is worn by the patient. Alternatively, a whitening strip may be inserted onto the teeth as the appliance is worn, or the strip may be placed into the appliance opposite the labial surface of these teeth.

A further advantage of the present invention is to provide a dental appliance having increased thickness between an upper shell and a lower shell and a system and a method for treating malocclusions which may provide a wire to be positioned buccally and labially around the outside of the appliance wherein the wire may be attached to the appliance, or may be snapped into the appliance by two or more ball and socket attachments or may be tied onto the appliance or slipped into tubes that are molded into the appliance. When the wire is expanded or constricted, the appliance may then move the teeth in the direction of the accessory wire.

A further advantage of the present invention is to provide a dental appliance having increased thickness between an upper shell and a lower shell and a system and a method for treating malocclusions which an imbedded wire may be molded into the buccal and labial and/or the lingual of the appliance that may be bent to enlarge (expand) or constrict the arch.

A further advantage of the present invention is to provide a dental appliance having increased thickness between an upper shell and a lower shell and a system and a method for treating malocclusions which may provide appliances in various arch shapes, such as square, tapered or normally shaped arches.

A further advantage of the present invention is to provide a dental appliance having increased thickness between an upper shell and a lower shell and a system and a method for treating malocclusions which may provide various anatomic alterations to the incisors to allow them to fit various racial differences inherent to teeth of people of, for example, Asian or African descent. In the case of Asians, an expanded area is provided at each side (mesial and distal) on the lingual surface to allow for a vertical bulge termed shovel-shaped incisor anatomy to fit so that these upper incisor teeth do not become labially displaced. In the case of the teeth of those of African descent, a more square anatomy to the incisors may be incorporated into the appliance.

A further advantage of the present invention is to provide a dental appliance having increased thickness between an upper shell and a lower shell and a system and a method for treating malocclusions which may provide an appliance that has one preformed slot for all the teeth which is very narrow labio-lingually in the area of the incisors; at the canine area in the upper and lower arches, the labio-lingual area slightly widens particularly at the midpoint of the canine and on the lingual of the canine; at the premolar area and/or the first and second deciduous molars, the appliance slightly widens and again widens at the area of the permanent molars. The appliance may be one size or several sizes for the deciduous, mixed and/or permanent dentition.

A further advantage of the present invention is to provide a dental appliance having increased thickness between an upper shell and a lower shell and a system and a method for treating malocclusions which may provide appliances that may be dispensed by a machine with or without a diagnostic program.

A further advantage of the present invention is to provide a dental appliance having increased thickness between an upper shell and a lower shell and a system and a method for treating malocclusions which may provide various sizes of appliances which may be measured with a single measure of one or more front teeth, e.g. at the end of a package or a paper or similar measure or by a ruler.

A further advantage of the present invention is to provide a dental appliance having increased thickness between an upper shell and a lower shell and a system and a method for treating malocclusions wherein the incisal edges are extremely thin labio-lingually and shaped so that any width of incisor tooth may be effectively moved and/or rotated by the appliance. The sockets are thin labio-lingually in the incisal half (upper half) for better tooth movement.

A further advantage of the present invention is to provide a dental appliance having increased thickness between an upper shell and a lower shell and a system and a method for treating malocclusions wherein the appliance has an upper and lower trough with labial, buccal and lingual margins or shields with an isthmus between the preformed sockets and/or slots for more than one tooth to accommodate teeth in a deciduous and/or mixed and/or permanent dentition. The margins may or may not cover a part of the gingival tissue. The canine sockets are sharp and pointed to accommodate any shaped canine.

A further advantage of the present invention is to provide a dental appliance having increased thickness between an upper shell and a lower shell and a system and a method for treating malocclusions wherein sockets of the dental appliance have interproximal ribs at the mesial and distal of each tooth to guide the teeth in eruption and move them mesial or distal along the arch.

A further advantage of the present invention is to provide a dental appliance having increased thickness between an upper shell and a lower shell and a system and a method for treating malocclusions wherein a labio-lingual thickness of a socket of the dental appliance is wider on the mesial than on the distal, which serves to move the incisors toward the midline.

A further advantage of the present invention is to provide a dental appliance having increased thickness between an upper shell and a lower shell and a system and a method for treating malocclusions which may provide extraction appliances wherein the interproximals of a dental appliance are removed at the extraction site, namely between the canine and second premolar sockets, while the interproximals between the canine and lateral and between the second premolar and first adult molar are increased, all of which aid in the closure of the extraction site.

A further advantage of the present invention is to provide a dental appliance having increased thickness between an upper shell and a lower shell and a system and a method for treating malocclusions which may provide extraction appliances wherein the upper first permanent molar socket is rotated so that the mesio-biccal cusp of this molar is rotated slightly lingually so that the molar is encouraged to be rotated in the finished case to occupy more room mesio-distally and keep the interproximal closed between the first upper molar and premolar, since the upper molar is trapezoid in shape.

A further advantage of the present invention is to provide a dental appliance having increased thickness between an upper shell and a lower shell and a system and a method for treating malocclusions which may have sharp projections descending inferiorly (downward) from the palatal area lingual to the incisors that discourage thumb sucking in an open-bite appliance design.

A further advantage of the present invention is to provide a dental appliance having increased thickness between an upper shell and a lower shell and a system and a method for treating malocclusions wherein a distal incisal edge of the canines (an increase in length and steepness of incline) of the dental appliance is accentuated to enhance incisal space closure by forcing the teeth to move toward the midline by the wedging effect from the canines on both sides of the upper and/or lower.

A further advantage of the present invention is to provide a dental appliance having increased thickness between an upper shell and a lower shell and a system and a method for treating malocclusions which may increase an upper labial cemento-enamel rib of a dental appliance that places pressure against the gingival ⅓ of the labial crown of the upper incisors to aid in lingual root torque of the teeth.

A further advantage of the present invention is to provide a dental appliance having increased thickness between an upper shell and a lower shell and a system and a method for treating malocclusions wherein molar sockets of a dental appliance may be squared with less rounded corners to be able to accept more unusually shaped molars, particularly those deciduous or permanent molars that are more square-shaped.

A further advantage of the present invention is to provide a dental appliance having increased thickness between an upper shell and a lower shell and a system and a method for treating malocclusions wherein a cingulum area of the upper incisor sockets of the dental appliance may be increased slightly to accept incisors with larger cingulum anatomy.

A further advantage of the present invention is to provide a dental appliance having increased thickness between an upper shell and a lower shell and a system and a method for treating malocclusions which may provide a dental appliance of any length to accommodate various mouths and for the comfort of the patient such as providing only an anterior appliance for the front teeth only.

A further advantage of the present invention is to provide a dental appliance having increased thickness between an upper shell and a lower shell and a system and a method for treating malocclusions which may utilize material, such as silicone, acrylic, or the like to the inside of the appliance in any area to increase the retainability or fit of the appliance as well as to stop further and/or any movement of teeth in this area.

A further advantage of the present invention is to provide a dental appliance having increased thickness between an upper shell and a lower shell and a system and a method for treating malocclusions which may have a varying amount of clearance for a gingival tissue or more slanted alveolar process in younger children who have permanent teeth still present in tissue that may have not yet erupted. This clearance allows the upper and/or lower margins to clear this tissue without digging into the tissue and avoids the need for preventive trimming of the appliance material to avoid pressure or digging into the tissue of the patient by the appliance margins.

A further advantage of the present invention is to provide a dental appliance having increased thickness between an upper shell and a lower shell and a system and a method for treating malocclusions which may have detachable upper and lower halves that may be detached by any means, such as, for example, a metal hinge whose leaves slip into slots at the rear end of the upper and lower halves.

A further advantage of the present invention is to provide a dental appliance having increased thickness between an upper shell and a lower shell and a system and a method for treating malocclusions which may have a hinging mechanism that may be molded into a separate upper and lower shell and may provide a dental appliance that may be very thin in the rear portion as well as the front section making it more comfortable and be able to allow the upper and lower to hinge together and spring apart with force.

A further advantage of the present invention is to provide a dental appliance having increased thickness between an upper shell and a lower shell and a system and a method for treating malocclusions which may have a thin hinge constructed from a stiffer material than the material of the upper shell and/or lower shell which is made of a softer material. The hinge may be stiff as well as forceful and may assist in maintaining a distance between the two halves with force, and without making the dental appliance thick and bulky. The dental appliance may maintain the relative position of the upper shell and the lower shell perfectly coordinated without distortion in a side-to-side movement and may maintain the front-to-back relation in perfect alignment without variation due to the stiffness of the hinge.

A further advantage of the present invention is to provide a dental appliance having increased thickness between an upper shell and a lower shell and a system and a method for treating malocclusions wherein preformed sockets and/or slots of the dental appliance may be designed for more than one tooth, to be arranged in a perfect intercuspation of teeth, or a super arrangement that advances or recedes the lower jaw slightly in relation to the upper teeth, with an ideal or modified arch shape, all of which will automatically straighten the teeth of a patient with passive wear and/or active biting wear to stimulate teeth to move and/or increase jaw movement and/or growth and/or restrict jaw movement and/or growth to be able to correct any of the problems of a malocclusion which include; but are not limited to, overbite, overjet, open-bite, molar and posterior teeth occlusion, arch changes, rotations, crowding, spacing, correction of temporomandibular function and/or problems, jaw relations and oral habits or malfunction.

A further advantage of the present invention is to provide a dental appliance having increased thickness between an upper shell and a lower shell and a system and a method for treating malocclusions which may have an upper and/or a lower margin to cover only the tooth areas to increase comfort.

A further advantage of the present invention is to provide a dental appliance having increased thickness between an upper shell and a lower shell and a system and a method for treating malocclusions wherein a design of the appliance with a mechanism for enabling the upper shell and the lower shell to be separate yet remain in contact may be made with prefabricated sockets or slots for more than one tooth or custom made from an actual model or digital representation of a patient's mouth by taking models, or obtaining the information by another source, such as from digital photos, x-rays, or the like or a combination of prefabricated (derived from standards of tooth sized and/or shapes) or customized (as derived directly from a specific patient).

A further advantage of the present invention is to provide a dental appliance having increased thickness between an upper shell and a lower shell and a system and a method for treating malocclusions wherein a measurement of a patient's size of teeth may be obtained by any means, such as, for example, with a ruler, or some sort of measure of widths and/or sizes of teeth and/or a single tooth or any combination to obtain a certain size of appliance.

A further advantage of the present invention is to provide a dental appliance having increased thickness between an upper shell and a lower shell and a system and a method for treating malocclusions wherein the appliance may be "U" shaped, and may have a tooth receiving trough with labial or buccal and lingual flanges with depressions between as individual tooth sockets or slots for more than one tooth, generally following the outline of the upper and/or lower teeth, which may or may not have interproximal ribs defining the outline of teeth.

A further advantage of the present invention is to provide a dental appliance having increased thickness between an upper shell and a lower shell and a system and a method for treating malocclusions which may provide appliances of various sizes to treat malocclusions and straighten the teeth at various ages in the deciduous, mixed and/or adult dentitions and either prevent problems, such as overbite, overjet, openbite, jaw relations, crowding, rotations, TMJ problems and such from developing and/or correcting the same problems.

A further advantage of the present invention is to provide a dental appliance having increased thickness between an upper shell and a lower shell and a system and a method for treating malocclusions which may control the eruption of teeth and/or depress certain teeth to correct overbite, gummy smiles, level the occlusion of teeth, properly intercuspate the teeth as in a correct bite, correct TMJ problems (temporomandibular problems) or the like.

A further advantage of the present invention is to provide a dental appliance having increased thickness between an upper shell and a lower shell and a system and a method for treating malocclusions which may straigthen incoming or erupting teeth prior to adult collagenous fiber formation and to hold them straight with the appliance or by any other retaining device while these fibers develop which can stabilize the result.

A further advantage of the present invention is to provide a dental appliance having increased thickness between an upper shell and a lower shell and a system and a method for treating malocclusions which may straighten the teeth sufficiently to avoid regular braces and/or other types of orthodontics at a later stage.

A further advantage of the present invention is to provide a dental appliance having increased thickness between an upper shell and a lower shell and a system and a method for treating malocclusions which may correct jaw relations whether the case is in an Angle Class I (normal jaw or molar relation), Class II (low jaw or molars back from a normal position), Class III (low jaw or molars forward in position).

A further advantage of the present invention is to provide a dental appliance having increased thickness between an upper shell and a lower shell and a system and a method for treating malocclusions wherein interproximal ribs between any combination of teeth are removed, allowing the teeth to be able to slip mesially or distally easily.

A further advantage of the present invention is to provide a dental appliance having increased thickness between an upper shell and a lower shell and a system and a method for treating malocclusions wherein the appliance can be manufactured with various resiliency and/or stiffness or a combination of both types of material to be more comfortable and/or more efficient in correcting certain problems, such as softer material in back for depression of molars in open corrections, or softer material in front for more comfortable tooth rotations, or the like.

A further advantage of the present invention is to provide a dental appliance having increased thickness between an upper shell and a lower shell and a system and a method for treating malocclusions which may treat any combination or number of deciduous, and/or permanent teeth and may be used in any combination with deciduous and/or permanent teeth present or absent in the mouth at anytime or during any period of eruption of exfoliation of any combination of teeth.

A further advantage of the present invention is to provide a dental appliance having increased thickness between an upper shell and a lower shell and a system and a method for treating malocclusions wherein an arrangement of the teeth within the dental appliance may be configured (a) beyond or (b) short of perfection depending on whether (a) an excessive overjet and/or receding jaw relation; or (b) protrusive dental and/or jaw relation is present to achieve a perfect result.

A further advantage of the present invention is to provide a dental appliance having increased thickness between an upper shell and a lower shell and a system and a method for treating malocclusions which may provide a dental appliance with varying arch widths that increase as the tooth sockets get larger. In this way, the arch size is increased when the teeth of a patient are larger and also if a patient with smaller teeth than the sockets, which may allow an arch to widen and/or expand making more room for crowding.

A further advantage of the present invention is to provide a dental appliance having increased thickness between an upper shell and a lower shell and a system and a method for treating malocclusions which may provide various sized appliances which may allow patients with smaller teeth, such as smaller deciduous teeth to wear a larger appliance with larger sized tooth sockets and a larger arch form. As a result, the size of the arch may be increased, and the space required as the larger adult teeth erupt into the arch may be increased to allow more room to prevent crowding from taking place.

A further advantage of the present invention is to provide a dental appliance having increased thickness between an upper shell and a lower shell and a system and a method for treating malocclusions which may provide a dental appliance having higher and thicker margins of the labio/buccal and lingual shields to better control the correction of cross-bites of the patient's teeth and to better control the eruption of the adult teeth.

A further advantage of the present invention is to provide a dental appliance having increased thickness between an upper shell and a lower shell and a system and a method for treating malocclusions which may provide a dental appliance that is large enough with a means for enabling the upper shell and the lower shell to separate as the user wears the dental appliance and opens his/her mouth, the dental appliance having higher margins which may prevent either aspiration of an appliance into the lungs, choking and/or swallowing of the dental appliance.

Additional features and advantages of the present invention are described in, and will be apparent from, the detailed description of the presently preferred embodiments and from the drawings.

BRIEF DESCRIPTION OF THE DRAWINGS

FIG. 18A illustrates a cross-sectional view of a dental appliance in an embodiment of the present invention taken generally along the line E-E.

FIG. 18B illustrates a cross-sectional view of a dental appliance in an embodiment of the present invention taken generally along the line E-E.

FIG. 18C illustrates a cross-sectional view of a dental appliance in an embodiment of the present invention taken generally along the line E-E.

FIG. 18D illustrates a cross-sectional view of a dental appliance in an embodiment of the present invention taken generally along the line E-E.

FIG. 18E illustrates a cross-sectional view of a dental appliance in an embodiment of the present invention taken generally along the line E-E.

DETAILED DESCRIPTION OF THE PRESENTLY PREFERRED EMBODIMENTS

The present invention relates to a dental appliance having increased thickness between an upper shell and a lower shell and a system and a method for treating malocclusions. The dental appliances may have an upper shell which receives the upper teeth of a user. The dental appliance may also have a lower shell which may receive the lower teeth of the user. The upper shell and the lower shell may, for example, be connected at a hinge. In addition, the upper shell and the lower shell may be connected by any other means which may enable the upper shell and the lower shell to be separate bodies yet remain in contact and maintain the relative position of the upper and lower halves constant from front to back and from side to side. Moreover, a thickness between the upper shell and the lower shell may be sized to allow positioning of the dental appliance further rearward into a mouth of a user than demonstrated in known dental appliances. In addition, a hinge portion of the dental appliance, or other connecting means, may be sized to extend treatment of malocclusions to the rear teeth of a user and/or to assist in alignment of a jaw of the user.

Figure 1:
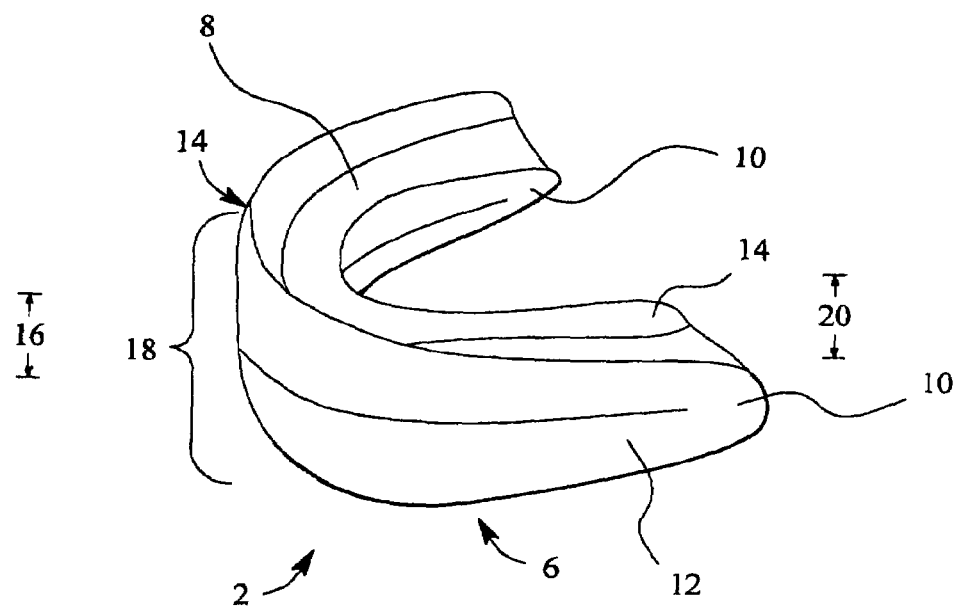
FIG. 1 illustrates a top perspective view of a dental appliance in an embodiment of the present invention.

Referring now to the drawings, wherein like numerals refer to like parts, FIG. 1 illustrates a dental appliance 2 having an upper shell 4 and a lower shell 6. The upper shell 4 may have a flat occlusal surface 8. The lower shell 6 may also have a flat occlusal surface (not shown). Both the upper flat occlusal surface 8 and/or the lower occlusal flat surface may accommodate various teeth having variations in cuspal and/or groove anatomy without interference. The upper shell 4 and the lower shell may be attached, for example, at a hinge portion 10 or by other means. A buccal shield 12 may provide an outer boundary or wall for the dental appliance 2 and a lingual shield 14 may provide an inner boundary or wall for the dental appliance 2.

The dental appliance 2 may have a first thickness 16 between the upper shell 4 and the lower shell 6 at a front portion 18 of the dental appliance 2 which receives incisors. The thickness 16 may be sized to stimulate masseter muscles of a user when the dental appliance 2 is worn. Specifically, the thickness 16 between the upper shell 4 and the lower shell 6 may assist a user in maintaining the dental appliance 2 within the mouth while sleeping. In addition, the dental appliance 2 may provide a force against a dentition of the user to increase depressive forces against maxillary (upper) and mandibular (lower) incisors and canines. As a result, the dental appliance 2 may assist in correcting an excessive overbite. Moreover, as the thickness 16 is increased, the dental appliance 2 may increase automatic triggering of a closing musculature.

The hinge portion 10 may have a second thickness 20 between the occlusal surface 8 of the upper shell 4 and an occlusal surface (not shown) of the lower shell 6. The thickness 16 between the upper shell 4 and the lower shell 6 which receive the incisors may or may not be equal to the thickness 20 of the hinge portion 10. Preferably, the first thickness 16 is greater than the second thickness 20, especially in cases in which the dental appliance 2 may treat overbite. The first thickness 16 and the second thickness 20 may be sized to enable the dental appliance 2 to be positioned close to a rear of the mouth of the user when worn. The first thickness 16 and the second thickness 20 may be sized to enable the dental appliance 2 to be worn further within the mouth of the user than known dental appliances.

Figure 2:
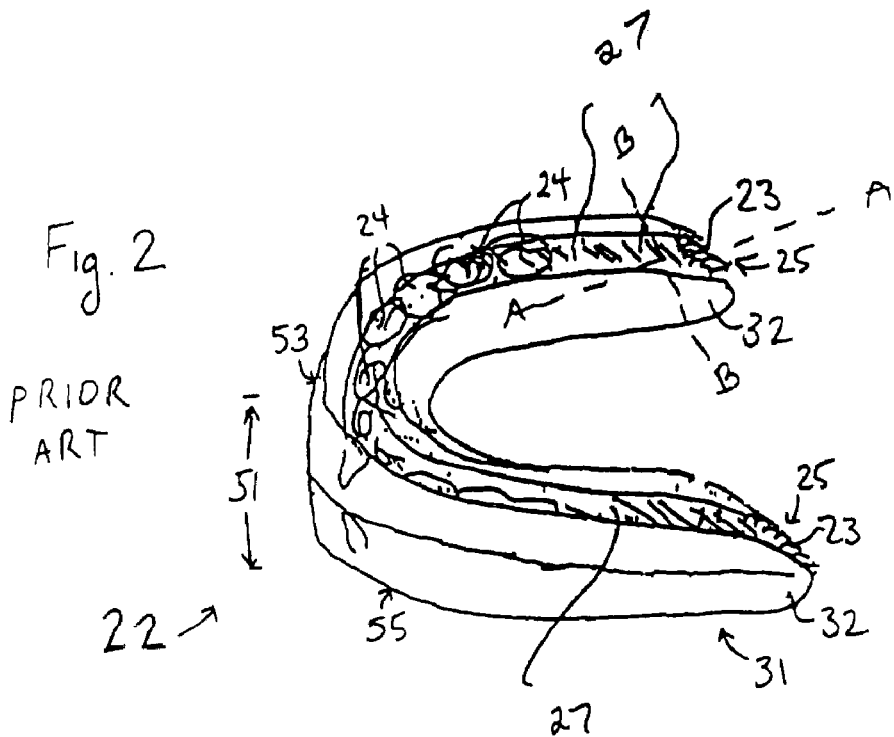
FIG. 2 illustrates a top perspective view of a known dental appliance.
Figure 4A:
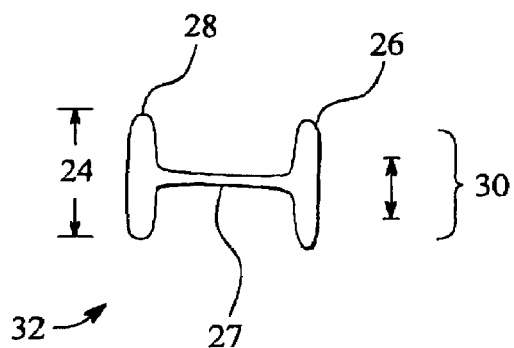
FIG. 4A illustrates a cross-sectional view of a hinge portion of a known dental appliance taken generally along the line B-B.
Figure 4B:
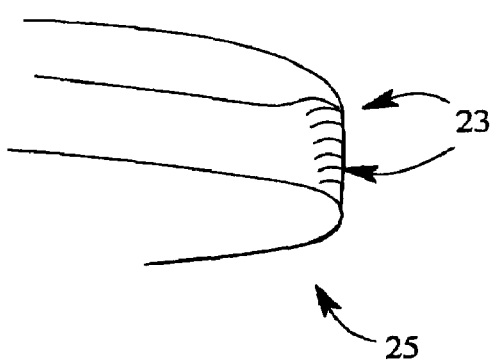
FIG. 4B illustrates a top perspective view of a hinge portion of the dental appliance in FIG. 2 taken generally along the line A-A.

FIG. 2 illustrates a known dental appliance 22. The dental appliance 22 has sockets 24 for receiving individual teeth of a user. The dental appliance 22 also has an isthmus 27 between a lingual shield 26 and a buccal shield 28. The isthmus 24 has a reduced thickness 30 at a hinge portion 32 or, in other known embodiments, at a most rear area of a dental appliance at which an upper shell and a lower shell are fixed together. For example, the thickness 30 is often less than one millimeter. FIG. 4A provides a cross-sectional view of the hinge portion 32 generally taken along the line B-B. As previously stated, the reduced thickness 30 of the dental appliance 22 is intended to encourage eruption of rear teeth, but requires a stabilizing rib 23 across a distal end 25 to provide strength to the isthmus 27. FIG. 4B illustrates a partial top view of the distal end 25 of the dental appliance 22. The dental appliance 22 prevents complete eruption of the rear tooth and does not allow complete treatment of a malocclusion. Moreover, the reduced thickness 30 prevents a rear portion 31 of the dental appliance 22 from covering an entire occlusal surface of a last molar. As a result, only a portion of the last molar is corrected by the dental appliance 22. An uprightness of the molar is also affected by a tipping action of the dental appliance on the last tooth; specifically, a depressing of movement of the last tooth by the rib 23.

Figure 3:
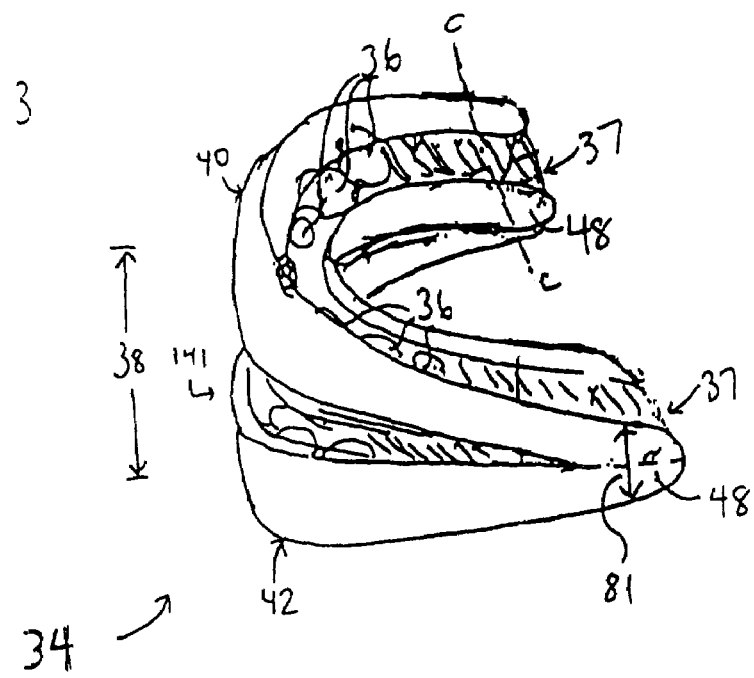
FIG. 3 illustrates a top perspective view of a dental appliance in an embodiment of the present invention.
Figure 5:
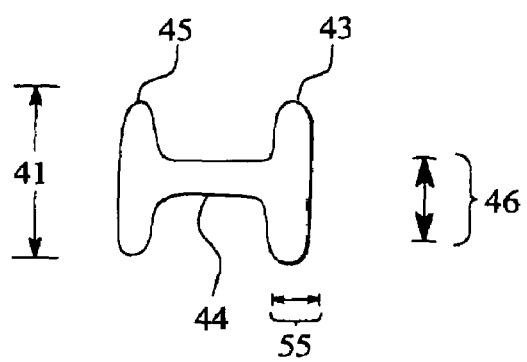
FIG. 5 illustrates a cross-sectional view of a hinge portion of the dental appliance in FIG. 3 taken generally along the line C-C.

FIG. 3 illustrates a dental appliance 34 of the present invention. The dental appliance 34 may have sockets 36 for receiving individual teeth of a user or may have slots for more than one tooth. The sockets 36 or slots may be made from impressions of a specific patient's mouth. The sockets 36 and/or slots may also be made from statistical standards of shapes and/or sizes of groups of teeth arranged in an ideal arrangement to be used in deciduous, mixed, and/or adult dentitions. Also, the dental appliance 34 may have an increased thickness 38 between an upper shell 40 and a lower shell 42, in an area of the upper shell 40 and the lower shell 42 which may receive the incisors, than demonstrated in the dental appliance 22 of FIG. 2. In addition, the dental appliance 34 may have an isthmus 44 which may have an increased thickness 46 at, for example, a hinge 48 or other means of connecting the upper shell 40 and the lower shell 42 wherein the upper shell 40 and the lower shell 42 are separate bodies yet remain in proper relation to each other from side-to-side and from front to back. The thickness 46 of the isthmus 44 may be greater in comparison to the thickness 30 of the isthmus 24 illustrated in FIG. 2. A cross-sectional view of the isthmus 44 taken generally along the line C-C is provided in FIG. 5.

The increased thickness 46 of the isthmus 44 may allow the posterior margins to be thicker and provide more force for tooth movement in the rear portion of the mouth in spite of the resilient material from which the dental appliance 34 is constructed and remain comfortable to a user, particularly in the front of the mouth where the margins may be thinner. Moreover, the increased thickness 46 of the isthmus 44 may eliminate a need for the rib 23 of the dental appliance 22 of FIG. 2 at the distal end 25. The increased thickness 46 of the isthmus 44 may also enable a distal end 37 of the dental appliance 34 to proceed further rearward into the mouth of the user. The distal end 37 may then cover and support an entire crown of the last molar for a user having a mixed dentition, a deciduous dentition or a full adult dentition.

Referring to FIG. 4A, the lingual shield 26 and the buccal shield 28 have a height 29. At a distal end 25, the height 29 of the buccal shield 28 and the lingual shield 26 is reduced because of the reduced thickness 30 of the isthmus 24 and an inability of the dental appliance 22 to proceed as far rearward into the mouth of the user as the dental appliance 34. However, the dental appliance 34 of FIG. 3 may have an increased height 41 for a lingual shield 43 and a buccal shield 45 because of the increased thickness 46 of the isthmus 44. A thickness 55 of the lingual shield 43 and the buccal shield 45 may also be increased. As a result, the dental appliance 34 may have increased strength to support the lingual shield 43 and the buccal shield 45. Moreover, the dental appliance 34 may be positioned further rearward into the mouth of the user than demonstrated in known dental appliances. Moreover, the dental appliance 34 may control a buccal movement and/or a lingual movement of the last molar and/or a tooth adjacent to the last molar. Control of the buccal movement and/or the lingual movement may enable a molar crossbite or a constricted or wide upper/lower arch to be better controlled and/or treated. Control of the buccal movement and/or the lingual movement may also enable complete correction of a bilateral crossbite, or scissor bite. In an embodiment, a greater height 41 of the lingual shield 43 and the buccal shield 45 and/or a greater thickness of the lingual shield 43 and the buccal shield 45 may enable the dental appliance 34 to control cross-bites in a posterior area and/or control eruption of molars more efficiently then demonstrated in the dental appliance 22.

In addition, the hinge 48, or other connecting means, may provide greater resistance in closing, as well as lateral movement, due to the increase in height 41 and the thickness 55 of the lingual shield 43 and the buccal shield 45. The hinge 48 may also guide a lower jaw of the user to close in a proper forward position without producing a distortion antero-posteriorly which may be critical to treatment of overjet and molar relations. Further, the hinge 48 may provide increased lateral control of the lower jaw, enabling proper intercuspation and lateral coordination of an upper jaw and the lower jaw to promote a proper bite. Also, the hinge 48, or any other hinging mechanism, may enable proper correction of midlines at a front of the mouth of the user, as illustrated in FIG. 6B at line G-G.

In an embodiment, the dental appliance 34 when worn may proceed rearward to cover a first deciduous molar of a user having a deciduous or mixed dentition. In another embodiment, the dental appliance 34 may be designed to proceed rearward to cover a second deciduous molar of a user with a deciduous or mixed dentition. In yet another embodiment, the dental appliance 34 may be designed to proceed rearward to cover a first permanent molar of a user also having a mixed dentition, or a permanent dentition, or cover a second permanent molar in an adult dentition.

In an embodiment, the appliance 34 may be molded in a wide-open position which may strengthen the springiness of the hinge. As a result, the dental appliance 34 may be more likely to open as the mouth opens. In another embodiment, the dental appliance 34 may be molded by placing a metal plate at a parting line (not shown) to prevent the upper shell 40 and the lower shell 42 from being molded together. In another embodiment, the dental appliance 34 may be cut with, for example, a saw or knife to shape the upper shell 40 and the lower shell 42. The dental appliance 34, when molded in a closed position, may be opened and held in an open position while a material the dental appliance 34 is constructed from cools. In another embodiment, the hinge 48 of the dental appliance 34 may be opened, reheated and maintained in an open position while cooling.

The increased thickness 38 between the upper shell 40 and the lower shell 42, in an area of the dental appliance 34 of FIG. 3 which receives incisors, enables the dental appliance 34 to implement one or more types of hinge mechanisms, such as, for example, rubber hinges, metal plates, snaps, metal springs, repelling magnets or like mechanisms. Implementation of a hinge may not be possible in the dental appliance 22 of FIG. 2 because of a reduced thickness 51, 30 between an upper shell 53 and a lower shell 55, causing the hinge to be thin and/or weak. However, the dental appliance 34 of FIG. 3 may implement any type of hinge mechanism which may be heavy despite constructing the dental appliance 34 from a resilient material. As a result, the hinge may withstand an increased force of closure and/or may resist lateral movement of a lower jaw of a child. Moreover, the hinge may be implemented in the dental appliance 34 for treatment of malocclusions of users having deciduous dentitions, mixed dentitions, or adult dentitions. The dental appliance 34 may require resiliency to straighten the teeth without pain, but the hinge may require greater stiffness as a result of a thicker hinge, particularly for treating deciduous dentitions, mixed dentitions, or adult dentitions in which the user may provide increased force against the dental appliance 34 as an age of the user increases.

In cases in which a child or adult may wear the dental appliance 34 while sleeping and the child or adult sleeps on a side, a jaw of the child or adult may be pushed to one side with respect to an opposing jaw. A bulkier and larger sized hinge, or other connecting means, may resist movement of the jaw, prevent distortion of the dentition of the user and encourage more complete straightening of the teeth. Further, a resiliency of the dental appliance 34 wherein the hinge is more resistant to distortion due to the size of the hinge may be crucial to treatment of malocclusions of users, for example, of age five or older, where flexibility of the dental appliance 34 may be required.

The increased thickness 38 at a front 141 of the dental appliance 34 of FIG. 3, if increased beyond a normal amount beyond the thickness 46 of the rear portion 37 of the dental appliance 34 may assist in correcting an excessive overbite by encouraging eruption of back teeth and depression of front teeth. In an embodiment, the thickness 38 may be less than a normal amount than the thickness 46 of the rear 37 of appliance 34; as a result, the dental appliance 34 may assist in correcting an open bite wherein the back teeth are depressed, and the front teeth are allowed to erupt.

Figure 6A:
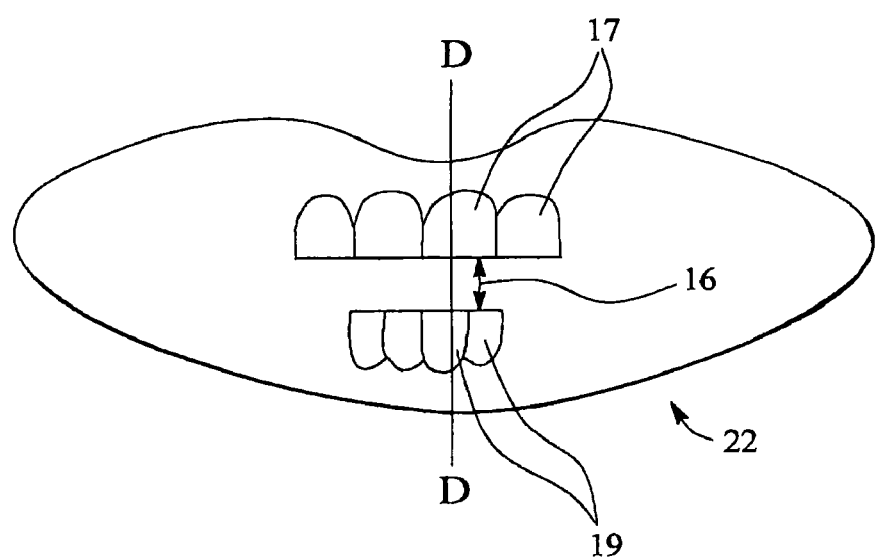
FIG. 6A illustrates a front plan view of the dental appliance in FIG. 2.
Figure 6B:
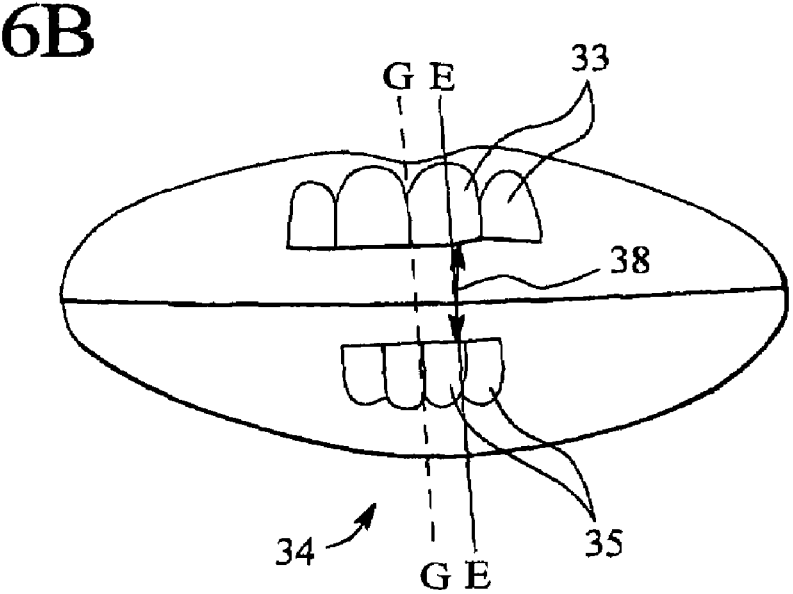
FIG. 6B illustrates a front plan view of the dental appliance in FIG. 3.
Figure 6C:
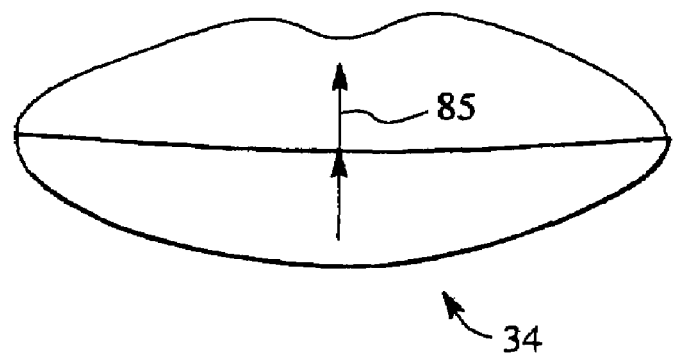
FIG. 6C illustrates a front plan view of the dental appliance in FIG. 3.

Referring now to FIG. 6A, a front plan view is provided of the dental appliance 22. The dental appliance 22 has a narrowed vertical distance 16 between incisal edges of upper incisors 17 and lower incisors 19. FIG. 6B illustrates the dental appliance 34 wherein the increased thickness 38 between the upper incisors 33 and the lower incisors 35 in an area which receives the incisors may allow an increase in overall bulk of the hinge 48 and the isthmus 44. FIG. 6C illustrates the dental appliance 34 wherein an arrow 85 may indicate a direction for proper placement of the dental appliance 34 within the mouth of the user.

Figure 7:
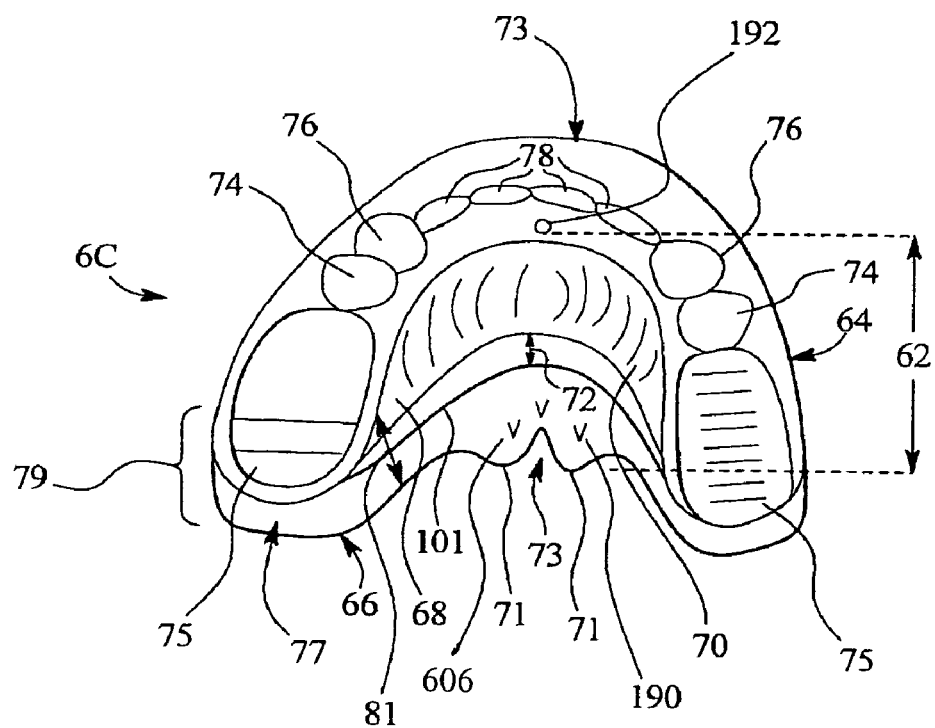
FIG. 7 illustrates a rear perspective view of a dental appliance in an embodiment of the present invention.

FIG. 7 illustrates a rear perspective view of a dental appliance 60 having an increased thickness 62 between an upper shell 64 and a lower shell 66. The increased thickness 62 enables a lingual surface 68 to have a concave portion 70 having an increased elevation 72 from a split line 101 at a front end 73 of the dental appliance 60. More specifically, the concave portion 70 may have a maximum height adjacent to sockets 74 for receiving first deciduous molars or first premolars; sockets 76 for receiving canines; and sockets 78 for receiving incisors. The concave portion 70 enables a tongue of the user to be placed within the mouth at an elevated position against a palate of an upper arch during resting posture. Moreover, the concave portion 70 prevents the tongue from being positioned at a lower position of a lower arch, which may be an abnormal position. By elevating the tongue of the user, the dental appliance 60 may cause expansion or widening of the upper arch.

In an embodiment, prongs or spikes 606 may beincorporated in the lingual surface 68 of the dental appliance 60 and may prevent the tongue from being pushed forward during swallowing or while at rest. A depressed area 192 may be positioned at the midline of the dental appliance 60, behind the sockets 78 and closer to the rear of the mouth. The depressed area 192 may serve as a guide for the user as to where to position the tongue during swallowing.

In addition, the dental appliance 60 of FIG. 7 may have lingual tabs 71 extending from the lower shell 66. A separation 73 may be provided between the lingual tabs 71 for a lingual midline frenum of a user. The lingual tabs 71 may extend laterally to assist in eruption and labial re-positioning of lingually-displaced lower lateral incisor teeth.

The dental appliance 60 may also have posterior slots 75 within the upper shell 64 and/or the lower shell 66. Because of the increased thickness 62 between the upper shell 64 and the lower shell 66, the posterior slots 75 may be longer mesio-distally than posterior slots in known dental appliances. As a result, the posterior slots 75 may properly accommodate posterior teeth of larger sizes, which may be a common variable in users. The posterior slots 75 may have a shovel-like shape at a distal end 77 of the dental appliance 60 and may taper flatly at the distal end 77 without requiring the distal rib 23 to provide additional strength to the isthmus 27 of the dental appliance 32. Despite the tapering of the posterior slots 75, a hinge portion 79 may maintain proper correction of the rear teeth of the user due to an increased thickness 81 of the hinge portion 79.

Figure 8:
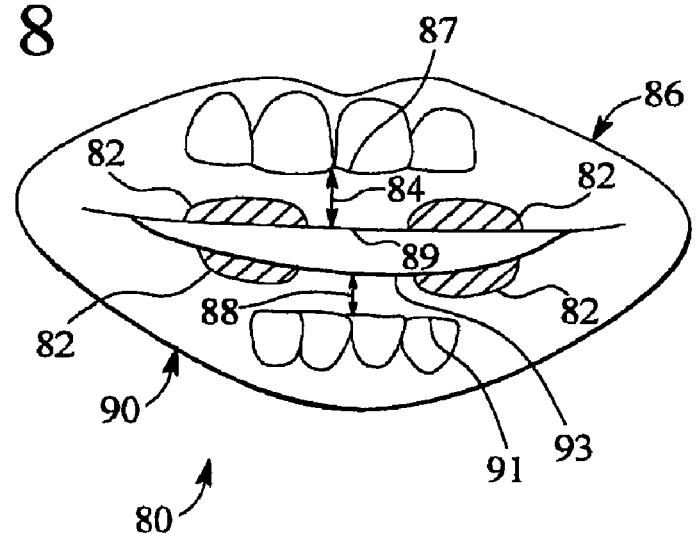
FIG. 8 illustrates a front plan view of a dental appliance in an embodiment of the present invention.

Referring now to FIG. 8, a front plan view is provided of the dental appliance 60 having breathing holes 82 preferably located in an anterior segment 73 of the dental appliance 60. Positioning of the breathing holes 82 in the anterior segment 73 is preferable for patients having, for example, asthma, allergies, or like medical conditions. The breathing holes 82 may enable a user to bite into the dental appliance 60 for an extended time while maintaining breathing. The dental appliance 60 may have a first increased thickness 84 in an upper shell 86 between an incisal edge 87 and a first parting line 89. Likewise, a lower shell 90 may have a second increased thickness 88 between an incisal edge 91 and a second parting line 93. The first increased thickness 84 may or may not be equal to the second increased thickness 88.

The first increased thickness 84 and the second increased thickness 88 may enable the breathing holes 82 to be sized larger than breathing holes placed in known dental appliances. As a result, the breathing holes 82 may not interfere with a vertical force provided by the dental appliance 60 towards the teeth of the user. The vertical force may be required to properly correct, for example, overbite and/or straighten the teeth of the user.

Figure 9:
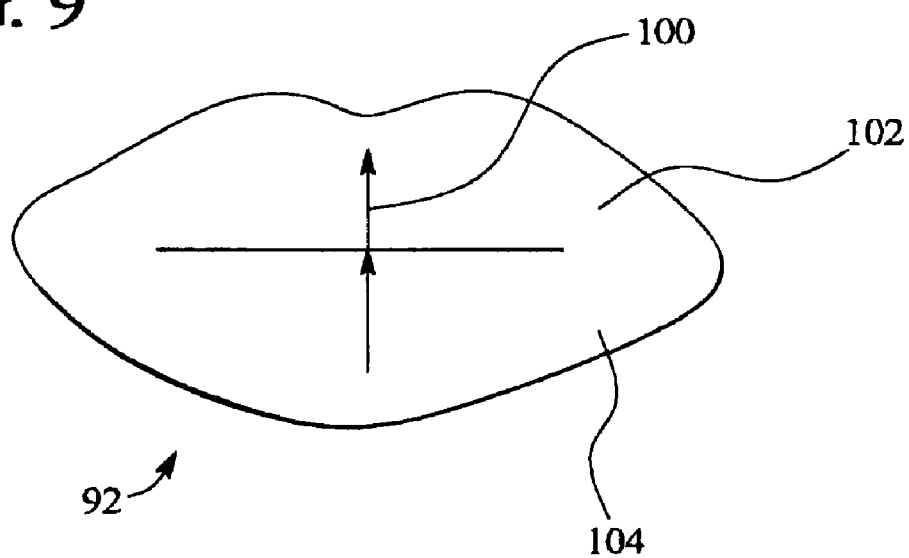
FIG. 9 illustrates a front plan view of a dental appliance in an embodiment of the present invention.

FIG. 9 illustrates a front plan view of a dental appliance 92. A line 100 molded into both an upper shell 102 and a lower shell 104 of the dental appliance 92 may indicate to the user a proper method of placing the dental appliance 92 within the mouth.

Figure 10A:
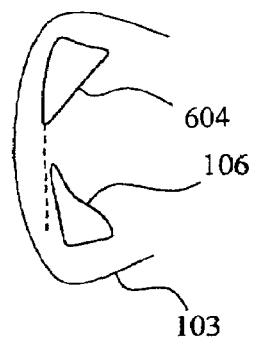
FIG. 10A illustrates a cross-sectional view of a stage of an occlusion of a user of a dental appliance in an embodiment of the present invention.
Figure 10B:
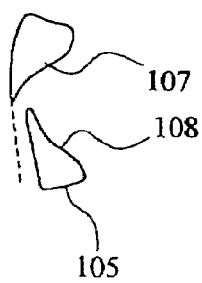
FIG. 10B illustrates a cross-sectional view of a stage of an occlusion of a user of a dental appliance in an embodiment of the present invention.
Figure 10C:
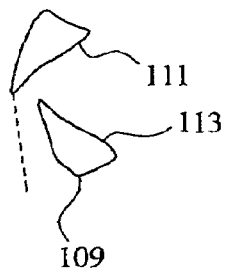
FIG. 10C illustrates a cross-sectional view of a stage of an occlusion of a user of a dental appliance in an embodiment of the present invention.
Figure 10D:
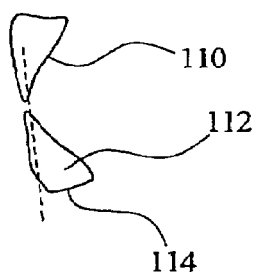
FIG. 10D illustrates a cross-sectional view of a stage of an occlusion of a user of a dental appliance in an embodiment of the present invention.
Figure 10E:
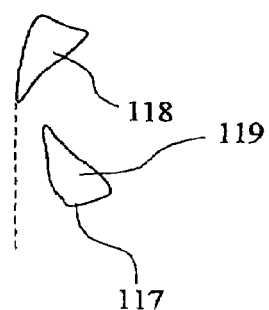
FIG. 10E illustrates a cross-sectional view of a stage of an occlusion of a user of a dental appliance in an embodiment of the present invention.

Referring now to FIGS. 10A through 10E, various tooth relations are provided for dental appliances which may treat users having different types of dentitions. Specifically, a dental appliance 150, such as that illustrated in FIG. 13, may treat a user having a permanent dentition and may have an almost end-to-end relation 103 of an upper incisor 604 and a lower incisor106 as illustrated in FIG. 10A. FIG. 10B illustrates an ideal incisor relation 105 which may be approximately 0.5 to 1.5 millimeters of overjet, in a front-to-rear distance, between an upper incisor 107 and a lower incisor 108 in a perfect dentition. In the use of a dental appliance 170, illustrated in FIG. 14 or appliance 190 in FIG. 15, which may treat a user having a mixed or deciduous dentition, an overjet relation of 1.0 millimeters to 2.5 millimeters as shown in FIG. 10C would be indicated. The younger the child, the more overjet would be indicated in the design of the appliance 170 or 190 in FIGS. 14 and 15 respectively. FIG. 10C. illustrates an incisor relation 109 between an upper incisor 111 and a lower incisor 113 in a dental appliance 170 or 190, illustrated in FIGS. 14 and 15, which may treat a user having a mixed or deciduous dentition. The relation 109 of the dental appliance 190 may have an overjet of, for example, one to 2.5 millimeters. An end-to-end relation 114 of an upper incisor 110 and a lower incisor 112 is illustrated in FIG. 10D.

In another embodiment, various arrangements of the teeth or jaw relations may be made or created by the dental appliance 103 such as slightly beyond perfection, as illustrated in FIG. 10A, to compensate for a case in which the dental appliance 103 is not worn in a full-time manner. FIG. 10B illustrates a perfect jaw relation 105. FIG. 10C illustrates a jaw relation 109 which may be short of perfection since the need of perfection is not recommended at younger ages when considerable lower jaw growth still remains. If the user is young and has several years of growth of the lower jaw remaining, a greater overjet configuration of the dental appliance 170 or the dental appliance 190 may be provided to the user.

In an embodiment, compensation may be required for a receding jaw of the user. Accordingly, an end-to-end jaw and tooth relation may be provided, such as that illustrated in FIG. 10D or even where the lower teeth 112 are positioned in front of the upper teeth 110 by 1 to 4 millimeters (not shown). In an embodiment, the patient or the user may require compensation for an overgrown lower jaw, referred to as a Class III, or mandibular protrusion. A dental appliance may be required which may provide a jaw relation 117 between an upper incisor 118 and a lower incisor 119, such as that illustrated in FIG. 10E, which may provide a greater overjet configuration to the user.

Figure 11A:
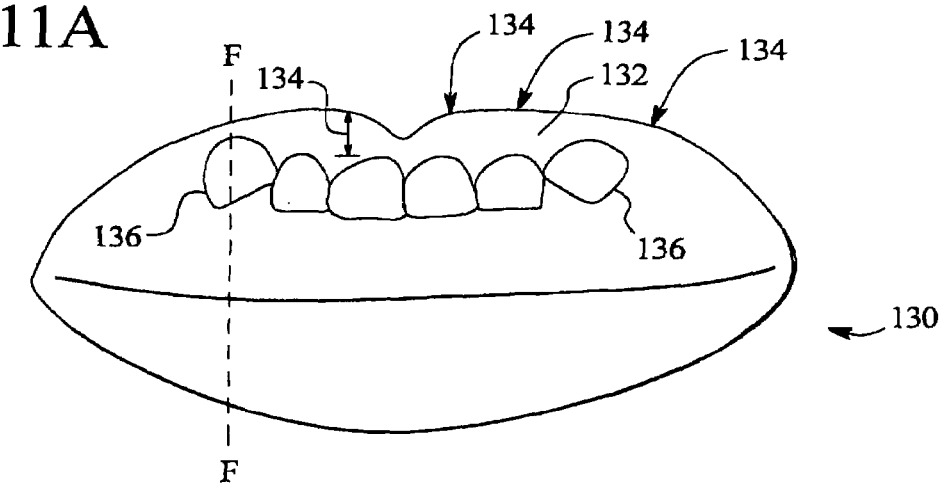
FIG. 11A illustrates a front plan view of a dental appliance in another embodiment of the present invention.
Figure 11B:
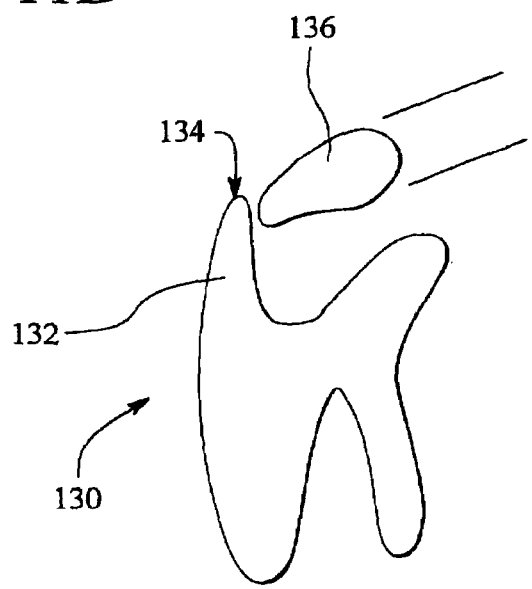
FIG. 11B illustrates a cross-sectional view of the dental appliance in FIG. 11A taken generally along the line F-F.

FIG. 11A illustrates a front plan view of a dental appliance 130 having an upper labial shield 132 which may have an extended height 134. Moreover, the upper labial shield 132 may extend distally through a canine 136, illustrated in cross-section in FIG. 11B, or further rearward into the mouth. The upper labial shield 132 may extend beyond an erupting canine 136 when the dental appliance 130 is worn. Accordingly, the upper labial shield 132 may contact high labially erupting canines and guide a tooth into the arch, which may assist in treating users with a mixed dentition or adult dentition who may have poorly erupting teeth.

In addition, the extended height 134 of the upper labial shield 132 may prevent a mandible of the user from slipping lingually as the mouth of the user is opened. As a result, the dental appliance 130 may assist in mandibular advancement and growth. The dental appliance 130 may also alter forward growth patterns of the upper jaw. In addition, the dental appliance 130 may assist in correcting overjet. Further, the dental appliance 130 may correct molar relations by causing the lower jaw to move forward while restraining the upper jaw. The lower jaw may then be held in a forward position until growth of the lower jaw stabilizes the lower jaw in the forward position.

Figure 12A:
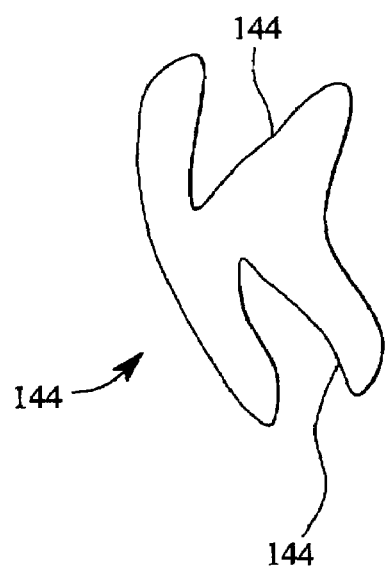
FIG. 12A illustrates a cross-sectional view of a known dental appliance taken generally along the line D-D.
Figure 12B:
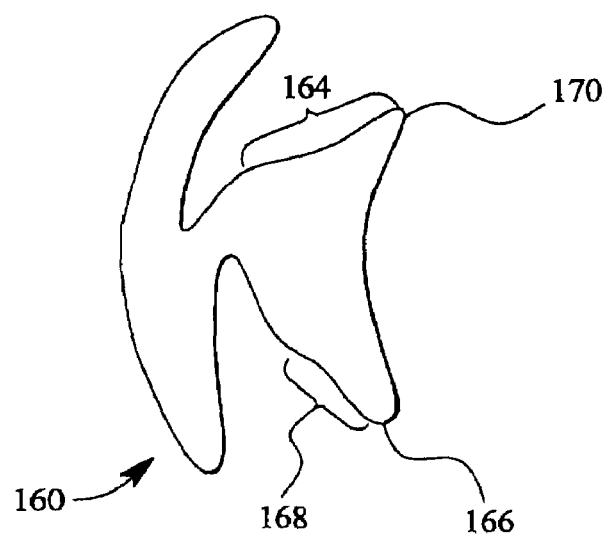
FIG. 12B illustrates a cross-sectional view of a dental appliance in an embodiment of the present invention taken generally along the line E-E.

FIGS. 12A and 12B illustrate a side cross-sectional view of a front portion of a known dental appliance 140 and a front portion of a dental appliance 160 of the present invention taken generally along the lines D-D and F-F, respectively. The known dental appliance 140 has a cemento-enamel junction elevated rim 144 which alters free eruption or tooth movement required for treatment of a malocclusion. In contrast, the dental appliance 160 may have a smooth area 168 in the lower lingual area 166 and have a smooth area 164 in an upper lingual area 170 which may be slanted more towards the lingual. The smooth area 168 and 164 may have a greater incline in a lingual direction; more specifically, toward an end portion 166 of a lower lingual margin and toward an end portion 170 of an upper lingual margin. The smooth upper area 164 and/or the lower smooth area 168 may provide a more graduated incline for lingually-positioned incisors and/or canines to be properly guided into a proper place in an arch.

Figure 13:
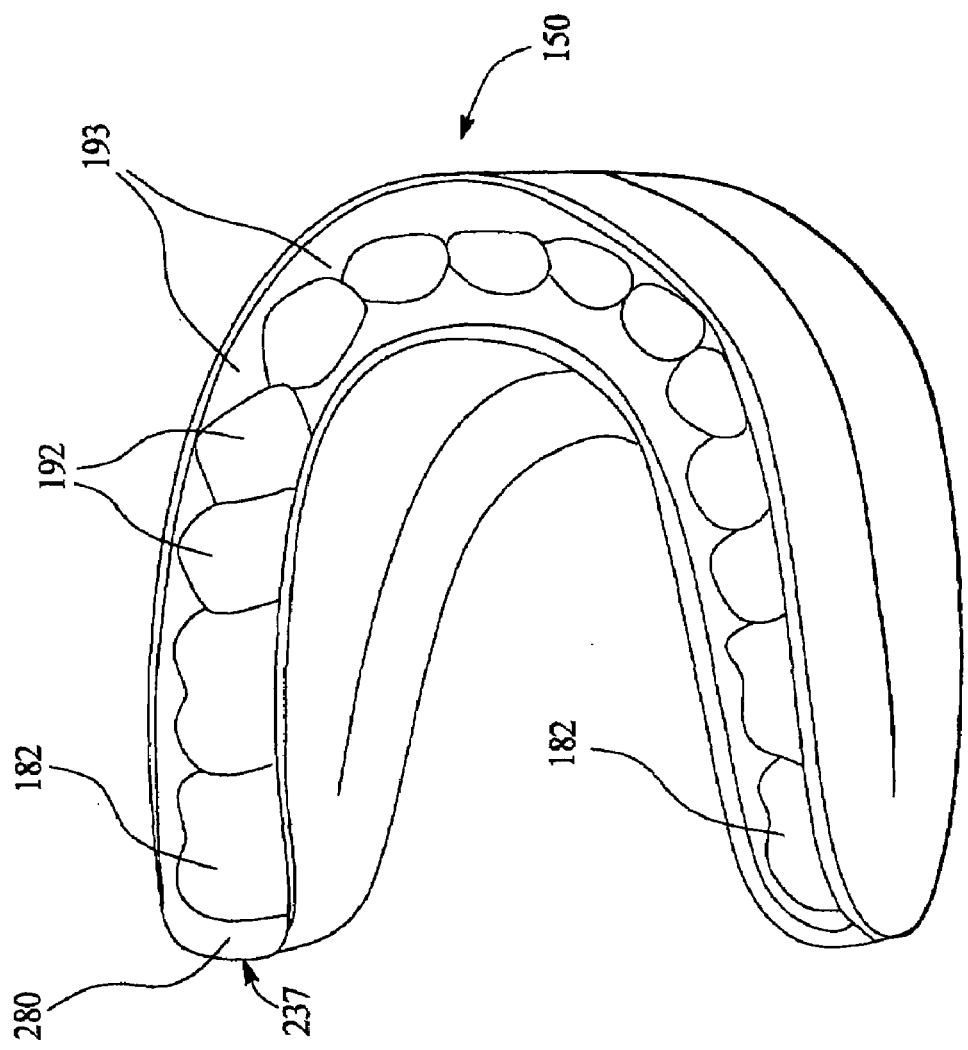
FIG. 13 illustrates a top perspective view of a dental appliance in an embodiment of the present invention.

FIG. 13 illustrates a dental appliance 150. The dental appliance 150 may have sockets 182 for receiving a last molar. In addition, the dental appliance 150 may have sockets 192 for receiving premolars. In an embodiment, the dental appliance 150 may be altered wherein an upper premolar on each side may be removed (not shown). In another embodiment, a lower premolar on each side may be removed (not shown). In another embodiment, four premolars may be removed, such as, for example, one premolar in each quadrant (not shown). A remaining premolar (not shown) in each of these embodiments may have a similar size and shape of a second upper premolar (not shown) and/or a second lower premolar (not shown) to accommodate either a first premolar or second premolar.

Figure 14:
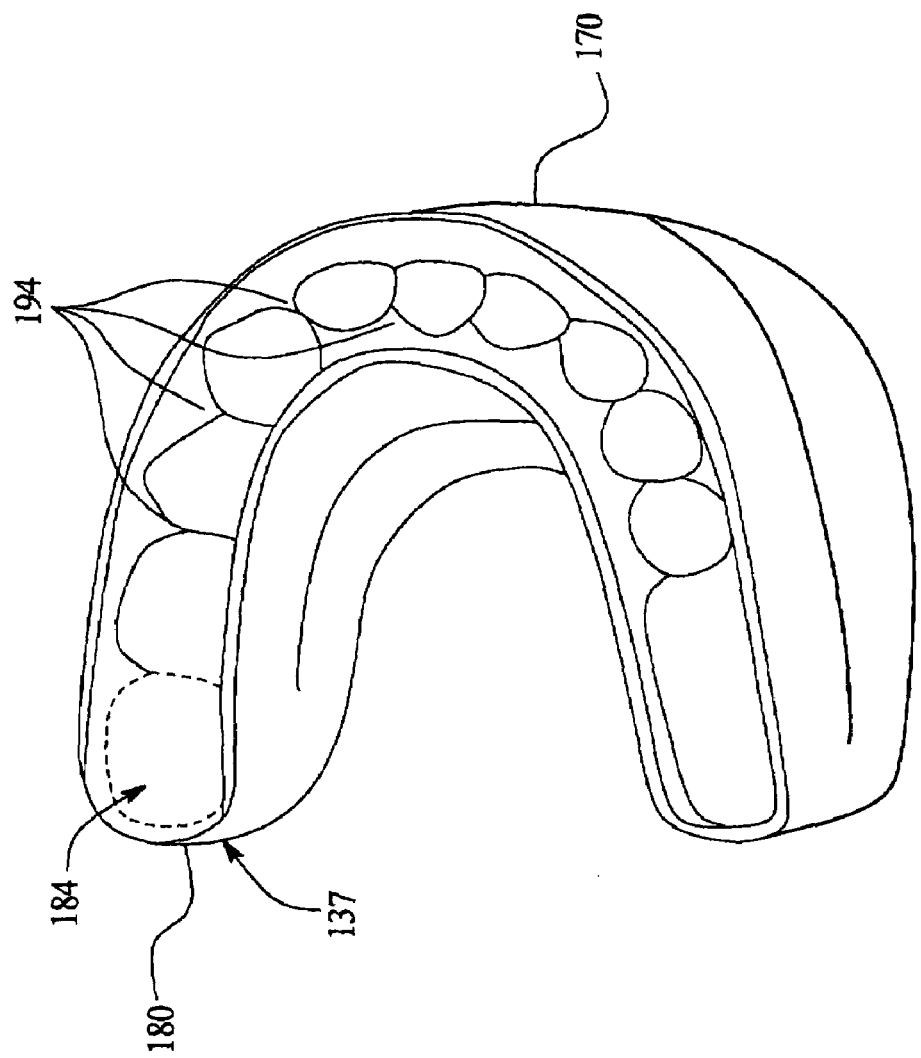
FIG. 14 illustrates a top perspective view of a dental appliance in an embodiment of the present invention.
Figure 15:
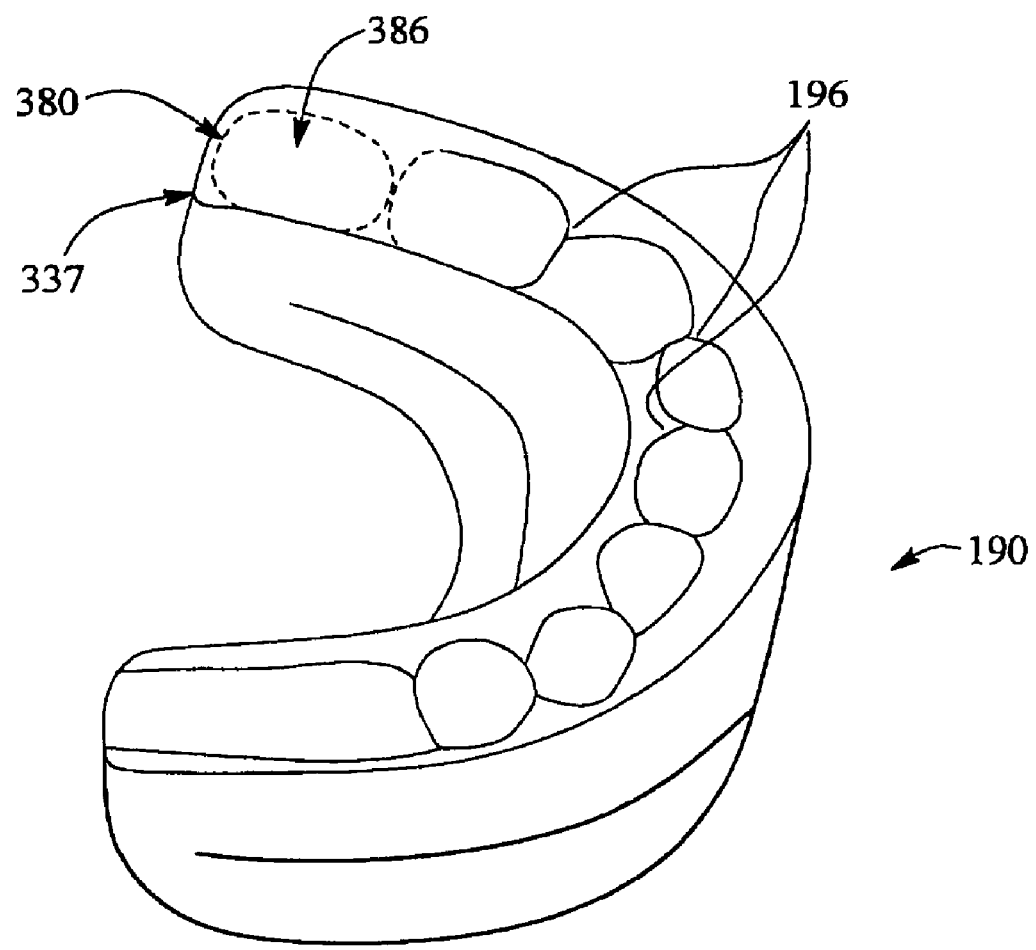
FIG. 15 illustrates a top perspective view of a dental appliance in an embodiment of the present invention.

FIG. 14 illustrates a dental appliance 170 which may have a hinge 137 having a greater thickness than known dental appliances. The hinge 137 may provide a sturdier mechanism for a patient of five or six years and older having, for example, a mixed dentition, and requiring a mixed dentition dental appliance. A thicker hinge 137 may also provide a sturdier mechanism for an adult patient having, for example, an adult dentition, and requiring an adult dentition dental appliance.

In general, older children and adults have stronger muscles for mastication and, as a result, chew and move their jaws with greater force. A larger, more massive hinge design may be required to resist side-to-side distorted movements as well as forward and backward displacements of the upper shell and the lower shell of a dental appliance. The sturdier hinge 48 may prevent such distortions to the dental appliance because the overall material of the appliance may be constructed from a resilient material to straighten rotated teeth without pain and discomfort to the user.

In addition, a thicker hinge 137 may provide a thicker or greater vertical distance 81 in the dental appliance 170. As a result, an isthmus 44 of the dental appliance 170 may be thicker 46 and may enable the dental appliance 170 to be positioned further toward the rear of the mouth wherein a distal end 180 may extend beyond the position of the last molar and a last molar slot 184 may contact the last molar of the patient. Further, the dental appliance 170 may prevent choking, aspiration or swallowing of the dental appliance. The distal end 280 of the dental appliance 150 may extend beyond a last molar enabling contact between a last molar slot 182 and the complete mesio-distal extent of the last molar of the patient. Likewise, the distal end 180 of the dental appliance 170 may extend beyond a last molar enabling contact between a last molar slot 184 and the complete mesio-distal extent of the last molar of the patient. In addition, the distal end 380 of the dental appliance 190 may also extend beyond a last molar, enabling contact between a last molar slot 386 and the complete mesio-distal extent of the last molar of the patient.

In another embodiment, a dental appliance 508 may have a hinging mechanism 500, illustrated in FIGS. 43A through 43E, that is constructed from a material separate from a remainder of the dental appliance 508. The material may be harder than the material forming the remainder of the dental appliance 508. In addition, the hinging mechanism may be imbedded into the material of the remainder of the dental appliance 508. The hinging mechanism 500 may be made of metal or plastic or the like.

Figure 43A:
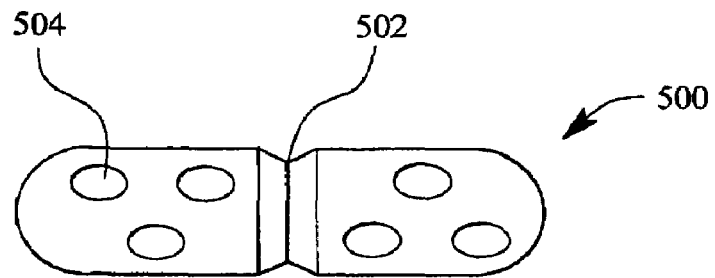
FIG. 43A illustrates a front plan view hinging mechanism for a dental appliance in an embodiment of the present invention.
Figure 43B:
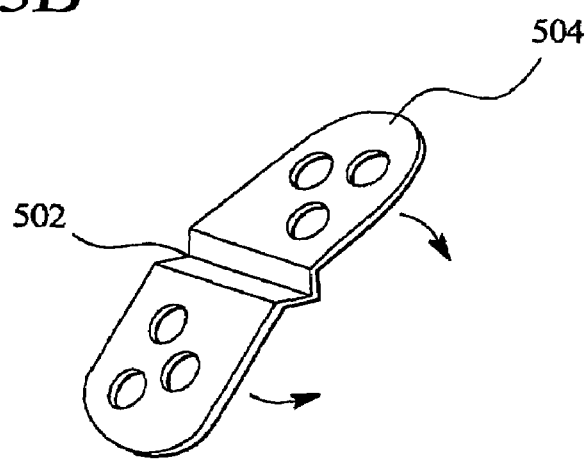
FIG. 43B illustrates a perspective view of the hinging mechanism in FIG. 43A.
Figure 43C:
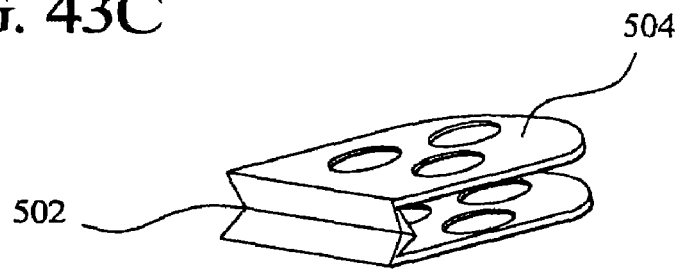
FIG. 43C illustrates a perspective view of the hinging mechanism in FIG. 43A.
Figure 43D:
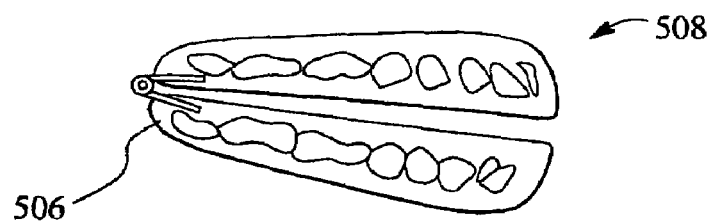
FIG. 43D illustrates a side view of the hinging mechanism in FIG. 43A implemented within a dental appliance in an embodiment of the present invention.
Figure 43E:
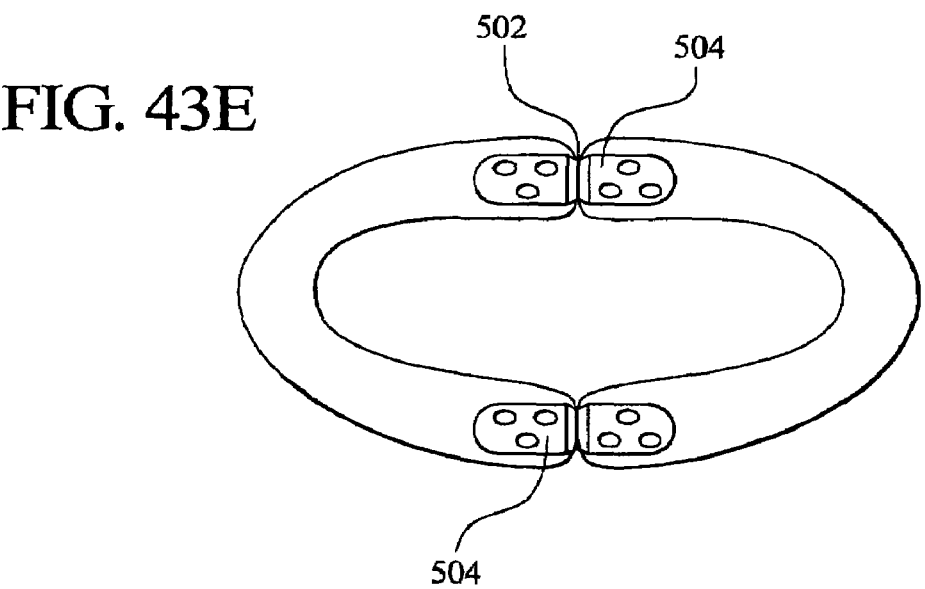
FIG. 43E illustrates a bottom plan view of the hinging mechanism in FIG. 43A implemented within a dental appliance in an embodiment of the present invention.
Figure 43F:
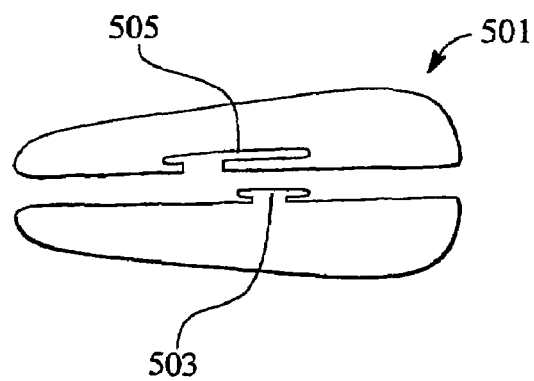
FIG. 43F illustrates a side view of a hinging mechanism in an embodiment of the present invention.

The hinging mechanism 500 may be made of, for example, polypropylene or like material. In an embodiment, the hinge mechanism 500 may have a living type hinge 502 and holes 504 to secure the hinge mechanism 500 to the dental appliance 508. In an embodiment, the dental appliance 508 may be molded. The molded, pliable material of an upper shell and a lower shell may project into the securing holes 504 of the hinge 500. In addition, the softer material of the upper shell and the lower shell may or may not be molded after placement of the hinge mechanism 500 adjacent to the dental appliance 500 to cover the living hinge portion 502 of the hinge 500 to create a unified one-piece appliance, as illustrated in FIG. 43D. This type of hinge 500 may enable the dental appliance 508 to have a shorter thickness 81 and/or a shorter thickness 38. As a result, the dental appliance 508 and the hinge mechanism 500 may be more comfortable to the patient. The dental appliance 508 may also project further into the mouth in a rearward direction with less material in a vertical direction.

Further, the living hinge 502 may be made stiffer or weaker by varying a thickness of a portion of the hinge 500 which may bend. The hinge 500 may be molded in an open position and also may be molded into the upper shell and the lower shell in an open position. This enables the hinge 500 to be stronger and to spring open with more force than a known hinge that is made of a softer material.

The hinging mechanism 500 has advantages of being more comfortable to the patient because the dental appliance 508 may be made significantly smaller in thickness vertically. The dental appliance 508 may be more durable than known dental appliances because of a resistance to breakage. Moreover, the dental appliance 508 may be soft and resilient; however, the dental appliance 508 may have a spring-like hinge that is of a stiff material and that may resume an open position more readily than known dental hinges constructed from softer materials. The dental hinge 500 may have a longer memory and may not become worn as quickly as demonstrated in known dental appliances, particularly under a higher temperature of the mouth.

Figure 41A:
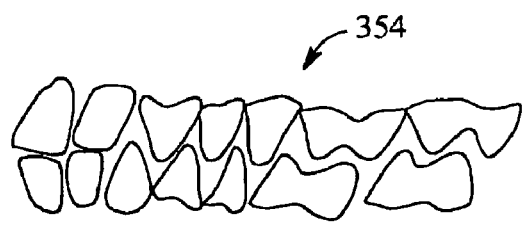
FIG. 41A illustrates a side view of tooth alignment resulting from use of a dental appliance in an embodiment of the present invention.
Figure 41B:
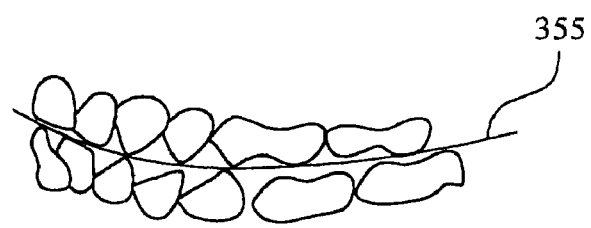
FIG. 41B illustrates a side view of an occlusion of an individual having a perfect overbite and a perfect overjet.
Figure 41C:
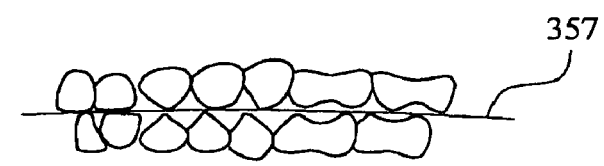
FIG. 41C illustrates a side view of an occlusion of an individual.
Figure 41D:
FIG. 41D illustrates a side view of an occlusion of incisors of an individual.

In an embodiment, a dental appliance may have sockets or slots arranged wherein a perfect intercuspated articulation 354 of an upper shell and a lower shell is created. Such an articulation is illustrated in FIG. 41A. A perfect overbite and overjet 356, such as that illustrated in FIG. 41D, may be produced automatically from the dental appliances 150, 170 190, and 508 illustrated in FIGS. 13, 14 15 and 43D respectively. Moreover, the dental appliances 150, 170, 190 and 508 may correct crowding, rotations or spacing, and may provide healthy temporomandibular joints without abnormal symptoms.

In an embodiment, a dental appliance may have any combination of sockets or slots for more than one tooth. Moreover, the dental appliance may be designed after obtaining models of a user. In an embodiment, the dental appliance may be partly or completely formed from standards of average tooth sizes or shapes and/or from models of a specific patient. In an embodiment, the dental appliance may be created from digital photos, video images, x-rays, or the like. In another embodiment, the dental appliance may be created from a computer-generated digital image. The dental appliance may have a hinge mechanism at a rear of the dental appliance as illustrated in FIGS. 3 and 43 D.

The dental appliances 150, 170, 190 and 508 illustrated in FIGS. 13, 14, 15 and 43D, respectively, may automatically straighten teeth of a user. Accordingly, the dental appliances 150, 170, 190 and 508 may be dispensed from a machine, either with a diagnosis by an individual or a computer program. In an embodiment, a user may independently determine an appropriate dental appliance by observing several examples and measuring his or her own teeth. The dental appliance may be dispensed by a machine or may be purchased over the counter.

In an embodiment, a user may measure his or her own teeth by measuring a front tooth or teeth from an image provided at an end of a box. In an embodiment, a paper measuring ruler may be provided with a packaging associated with the dental appliance. In another embodiment, the user may look into a mirror and a digital video camera or still camera may calculate a size of the teeth and may display the size on a monitor.

In an embodiment, the dental appliance 150, 170, 190 and 508 illustrated in FIGS. 13, 14, 15 and 43D, respectively, may be sized upon measuring the teeth of the user with a ruler. The user may measure widths of one to several teeth, either upper teeth or lower teeth, to obtain an estimate of the size of the required dental appliance.

Figure 44:
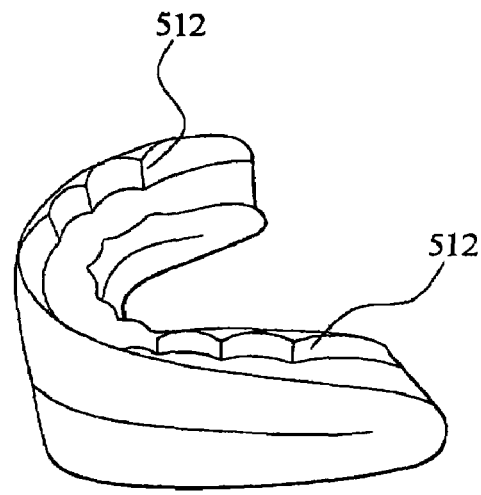
FIG. 44 illustrates a perspective view of a dental appliance in an embodiment of the present invention.

In another embodiment, a dental appliance may have a hinge mechanism that is generally U-shaped. In addition, an occlusal surface of the dental appliance may have individual tooth sockets and/or slots for more than one tooth. The dental appliance may also have a labial margin, a buccal margin and/or a lingual margin. Further, the dental appliance may have an isthmus connecting the labial margin, the buccal margin and/or the lingual margin which may have individual interproximal ribs 193, 194 and 196 for the teeth of the user or interproximal extensions in areas where teeth may be located in a slotted dental appliance 512 in which no individual sockets may be present, such as that illustrated in FIG. 44.

In an embodiment, the dental appliances 150, 170, 190 and 508 may have a hinging mechanism and may have various graduated sizes for treatment of different age groups. The dental appliances 150, 170, 190 and 508 may straighten the teeth and/or guide the teeth into the mouth while the teeth erupt. The dental appliance may also prevent and/or correct overbite, overjet, TMJ problems, open-bite, spacing, crowding and rotations. In addition, the dental appliance may control eruption of teeth or may enhance and/or encourage eruption and/or inhibit or discourage eruption and/or depress teeth. As a result, the dental appliance may prevent gummy smiles, overbite and may produce proper intercuspation 354 of teeth, and/or may properly level an occlusion 357 of teeth from a level of an improper occlusion 355.

Figure 38:
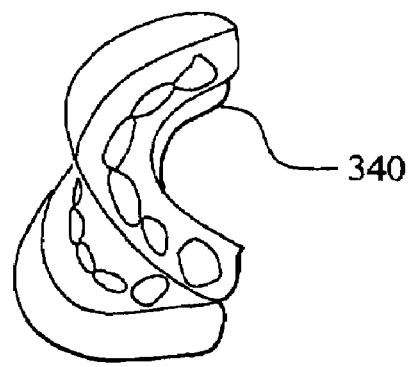
FIG. 38 illustrates a top perspective view of a dental appliance in an embodiment of the present invention.

In an embodiment, illustrated in FIG. 38, the dental appliance 340 may have a length to receive, for example, only an anterior or front section of an upper shell and/or a lower shell. The dental appliances 150, 170, 190 and 508 of FIGS. 13, 14, 15 and 43D, respectively, may also have a length to receive only an anterior or front section of an upper shell and/or a lower shell. In another embodiment, the dental appliances 150, 170, 190 and 508 may have various lengths (not shown).

Figure 16A:
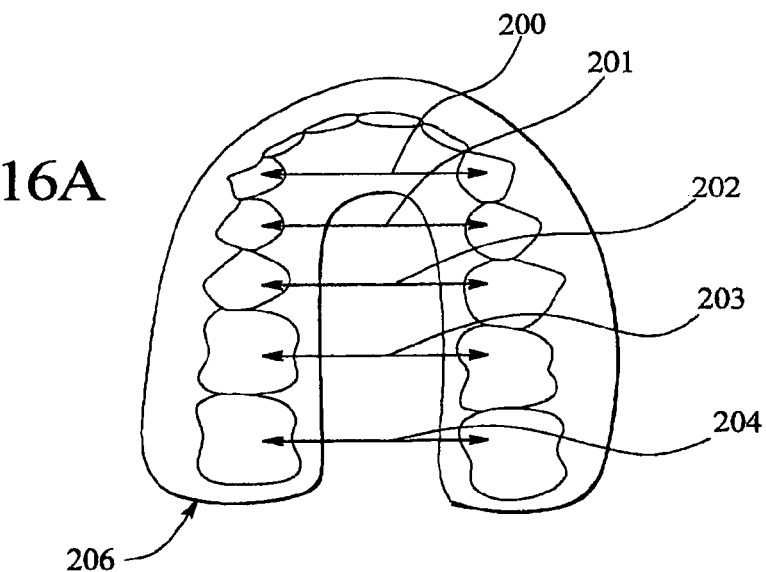
FIG. 16A illustrates a top plan view of a dental appliance in an embodiment of the present invention.
Figure 16B:
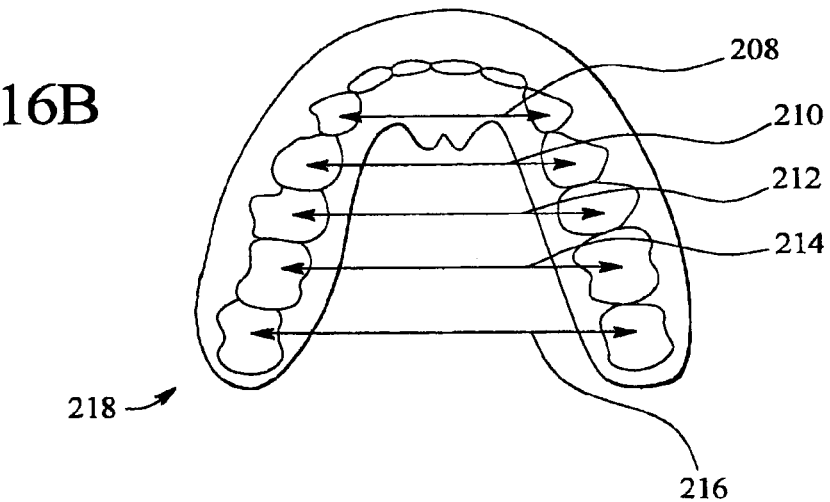
FIG. 16B illustrates a bottom plan view of a dental appliance in an embodiment of the present invention.

FIGS. 16A and 16B illustrate an upper shell 206 and a lower shell 218, respectively, of a dental appliance. The upper shell 206 may have arch widths 200, 201, 202, 203 and 204. The lower shell 218 may have arch widths 208, 210, 212, 214 and 216. In an embodiment, the arch widths 200, 201, 202, 203 and 204 of the upper shell 206 may be sized greater than the upper arch widths for the dental appliances 150, 170, 190 and 508 in FIGS. 13, 14, 15 and 43D as well as the normal sized arch widths 208, 210, 212, 214 and 216 of the lower shell 218. As a result, the dental appliance may correct a bilaterally constricted upper arch and bilateral and/or unilateral posterior cross-bite. In an embodiment, the arch widths 208, 210, 212, 214 and 216 of the lower shell 218 may be sized greater than the arch widths 200, 201, 202, 203 and 204 of the upper shell 206. The dental appliance may then correct a telescoping lower arch or scissor bite. The upper shell 40 and the lower shell 42 of the dental appliance 34 of FIG. 3 may be sized in manners similar to those described for the upper shell 206 and the lower shell 218. The dental appliance 34 may correct malocclusions, such as crossbites and/or scissor bites, as a result of the increased height 41 of the lingual shield 43 and the buccal shield 45 and/or the increased thickness 55 of the lingual shield 43 and the buccal shield 45. In an embodiment, widths 200, 201, 202, 203 and 204 of the upper shell 206 and the widths 208, 210, 212, 214 and 216 of the lower shell 218 may enlarge as the teeth of the user get larger and vice-versa. This, enlargement of the arches, however, may or may not be in coordination with tooth size. When only expansion of the arches is required, this coordination between arch size and tooth size may not be present.

In an embodiment, the arch widths 200, 201, 202 and 204 of the upper shell 206 and the arch widths 208, 210, 212, 214 and 216 of the lower shell 218 may be wider or narrower than normally demonstrated in arches of the user to enlarge or constrict both arches simultaneously.

Figure 17:
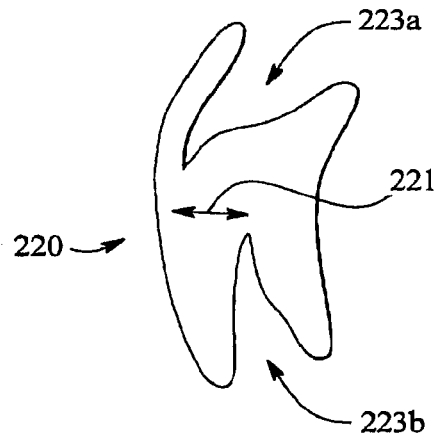
FIG. 17 illustrates a cross-sectional view of a dental appliance in an embodiment of the present invention taken generally along the line E-E.

FIG. 17 illustrates a cross-section of a front of a dental appliance 220. The dental appliance 220 may have an increased distance 221 between an upper jaw area 223a and a lower jaw area 223b. The dental appliance 220 may correct Class III jaw relations, commonly called protrusion or a forward position of the lower jaw in relation to the upper jaw, by moving the lower set of teeth 223b in a rearward position in relation to the upper set of teeth 223a which increases the distance 221.

FIGS. 18A through 18E illustrate various angulations of sockets for front teeth, namely, incisor areas of a dental appliance. FIG. 18A illustrates a normal angulation 222. FIG. 18B illustrates an angulation 224 in which incisors of the user may be more labially angulated. The angulation 224 may satisfy orthodontic philosophies, such as, for example, Bioprogressive group philosophies. FIG. 18C illustrates an angulation 226 which may have a more upright inclination than the angulation 222. FIG. 18D illustrates a normal angulation 228 for lower incisors. Further, FIG. 18E illustrates an angulation 230 which may have a more lingual crown inclination in comparison to the angulation 228.

Figure 19:
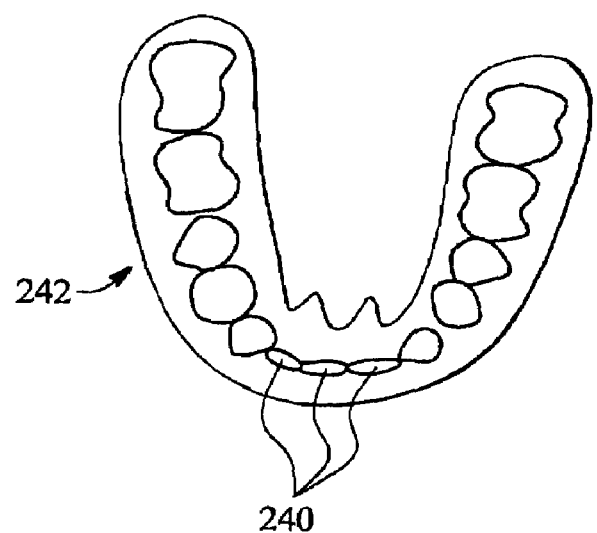
FIG. 19 illustrates a bottom plan view of a dental appliance in an embodiment of the present invention.

In an embodiment, the dental appliance 34 in FIG. 3 or the dental appliance 22 in FIG. 2 may have three lower incisors present in an appliance. FIG. 19 illustrates such an appliance 242 which may have three slots 240 for the lower incisors of the user. The appliances could be of the type for the adult dentition FIG. 13, the mixed dentition FIG. 14 or the deciduous dentition FIG. 15 or with additional hinging mechanisms such as those illustrated in FIGS. 40B and 43D.

Figure 20:
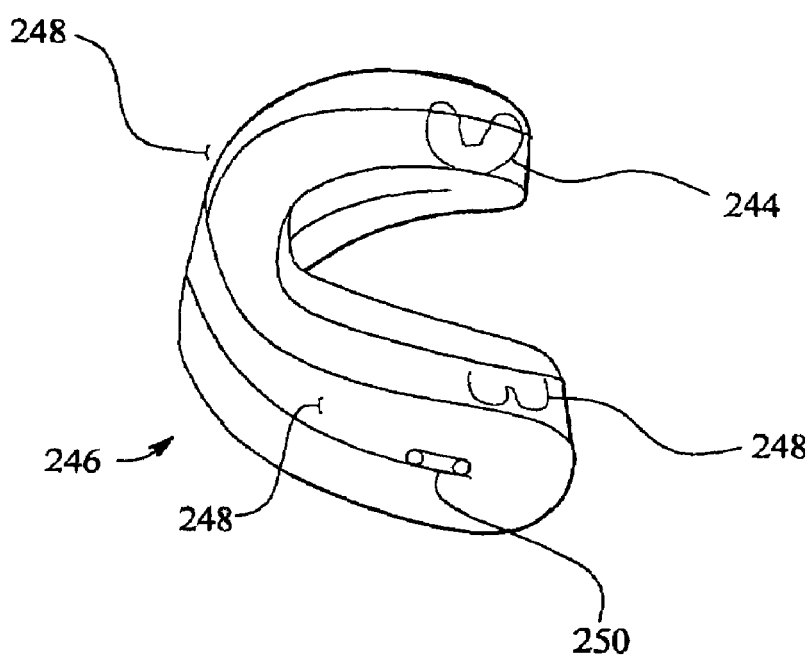
FIG. 20 illustrates a top perspective view of a dental appliance in an embodiment of the present invention.

FIG. 20 illustrates a dental appliance 246 which may have hooks 248 for attaching elastics, head gear or other devices within the mouth of the user. In an embodiment, the dental appliance 246 may have tubes 250 which may assist in securing a head gear appliance or accessory wires within the mouth of the user. Clasps 244 may be provided and may be constructed from metal, plastic or other material. The clasps 244 may be used to attach the dental appliance 246 to the mouth of the user.

Figure 21:
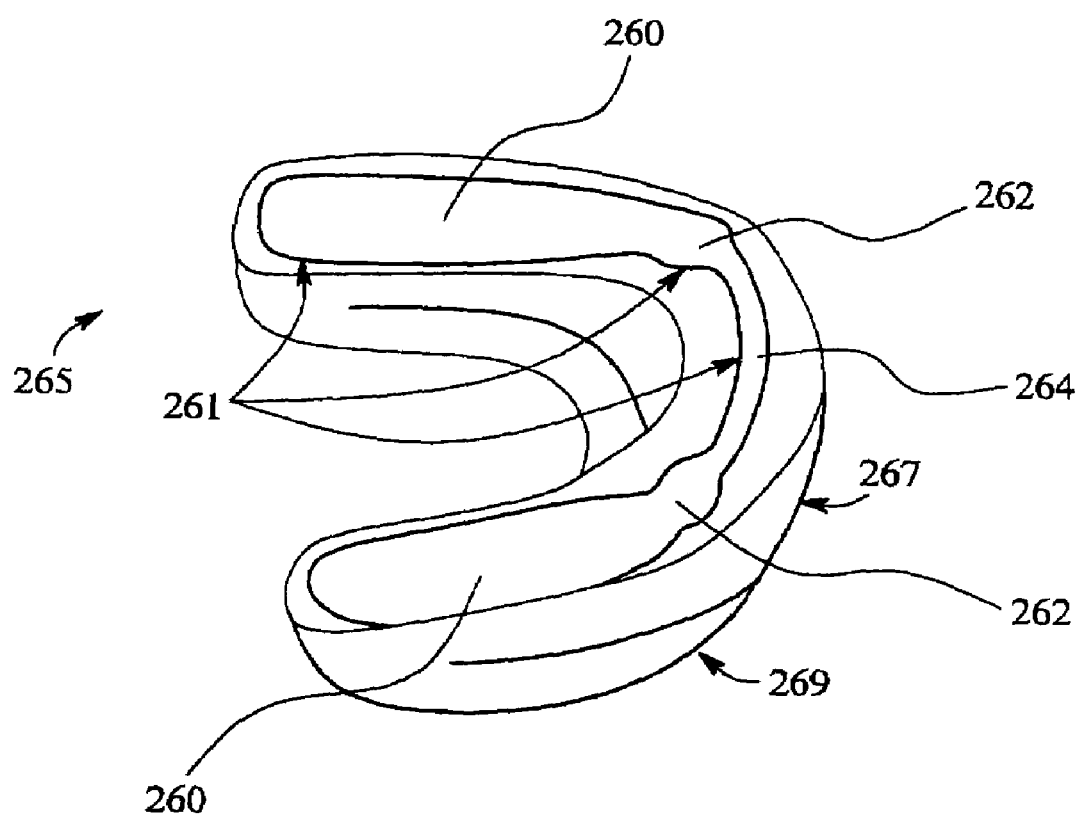
FIG. 21 illustrates a top perspective view of a dental appliance in an embodiment of the present invention.

FIG. 21 illustrates another embodiment of a dental appliance 265 which may have a single slot 261 and may have an area 260 for receiving posterior teeth. The slot 261 may narrow in an area 262 of the dental appliance 265 for receiving canine teeth. The slot 261 may also narrow in an area 264 for receiving incisor teeth. Each area 260, 262 and 264 varies in shape and/or size to adapt to the general anatomy of different types of the teeth of the user. The slot 261 may be in an upper shell 267 and/or a lower shell 269. In other embodiments, the dental appliance 265 may have any combination of slots and/or individual sockets in any number and/or location in the upper shell 267 and/or the lower shell 269.

Figure 22A:
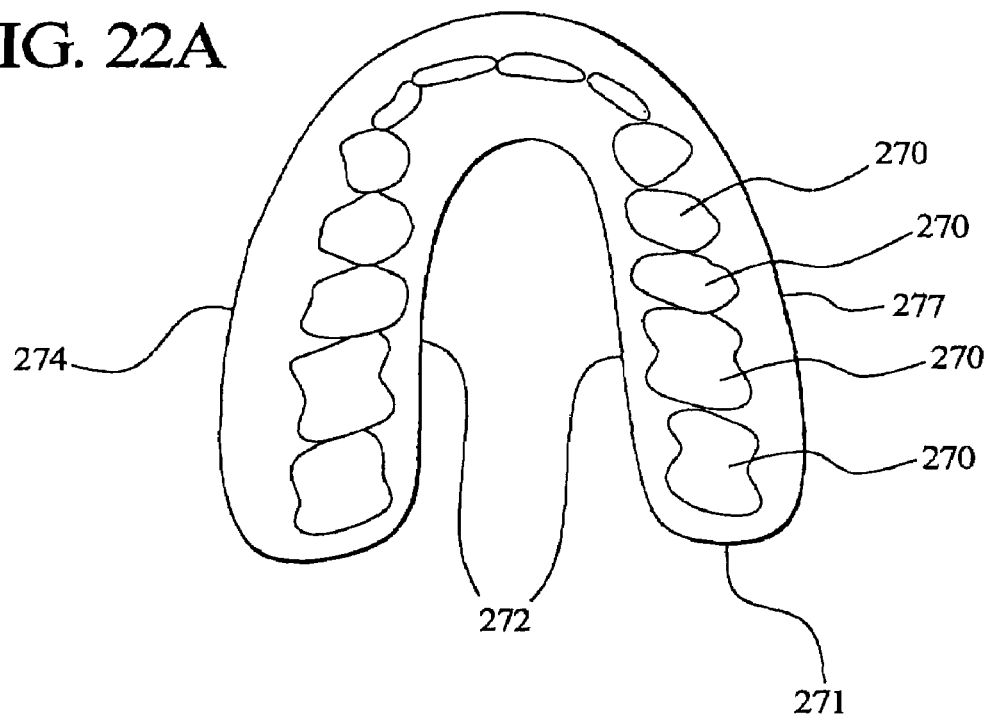
FIG. 22A illustrates a top plan view of a dental appliance in an embodiment of the present invention.
Figure 22B:
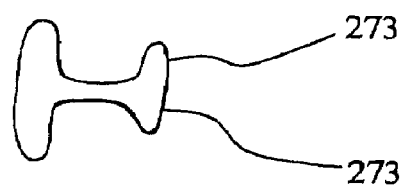
FIG. 22B illustrates a cross-sectional view of the dental appliance in FIG. 22A.
Figure 22C:
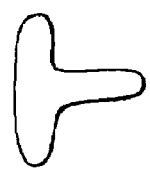
FIG. 22C illustrates a cross-sectional view of a dental appliance in an embodiment of the present invention.

FIGS. 22A and 22B illustrates a dental appliance 274 which may have a lingual shield 273 having a shorter length in the upper shell and/or the lower shell. In an embodiment, illustrated in FIG. 22C, no lingual shield is provided in the dental appliance 274. Such an embodiment may allow the tongue of the patient to exert an outward pressure against the upper teeth and/or the lower teeth and may cause expansion of the arch of the patient. In an embodiment, sockets 270 may be provided for teeth that are angulated toward a rear portion 271 of the dental appliance 274. A buccal shield 277 in the upper and/or lower arch may be expanded in a buccal direction. The dental appliance 274 may cause the upper and/or lower teeth to move buccally and may also distalize the teeth.

Figure 45:
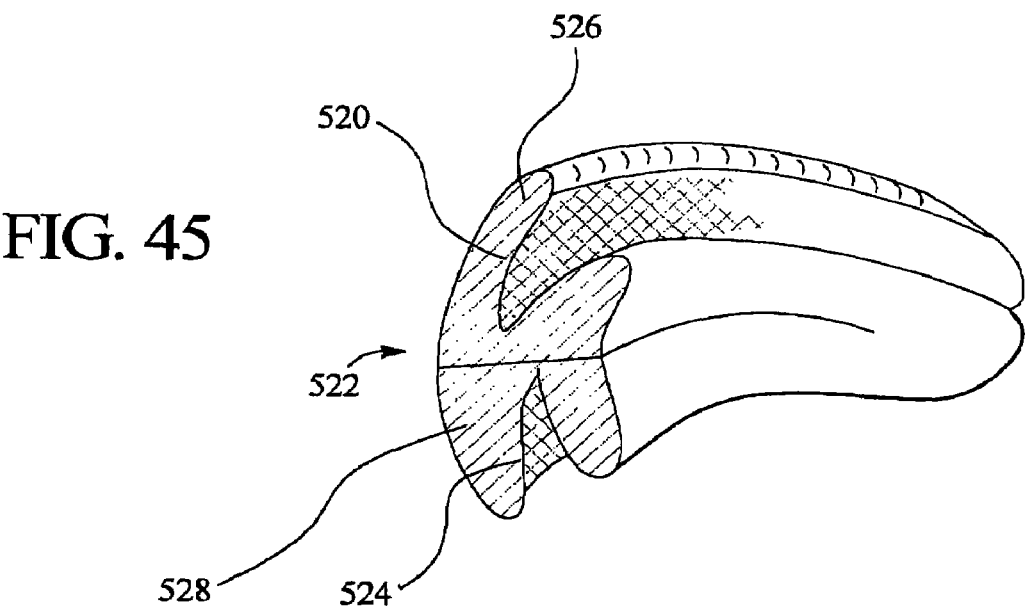
FIG. 45 illustrates a cross-sectional view of a dental appliance in an embodiment of the present invention.

In an embodiment, the dental appliances 150, 170, 190 and 508 in FIGS. 13, 14, 15 and 43D, respectively, may have a fluoride compound molded with the plastic or other material the dental appliance may be constructed from. In an embodiment, the dental appliances 150, 170, 190 and 508 may have a fluoride liquid placed into a socket or slot area of the dental appliance 150, 170 or 190. The fluoride may be absorbed by the material the dental appliance may be constructed from. When the dental appliance is worn by the user, the fluoride compound may leach out and may be absorbed by the teeth of the user. The dental appliance may then provide caries or cavity prevention. In another embodiment, a fluoride gel may be placed into the dental appliance prior to being worn. In another embodiment, a bleaching gel may be placed into the dental appliance to whiten the teeth of the user. In another embodiment, whitening strips may be placed on the teeth before inserting the dental appliance into the mouth. In an embodiment, illustrated in FIG. 45, a labial shield or shell of the upper 526 and/or lower 528 may be roughened on its interior or lingual surface 520 of the upper and on the lingual surface 524 of the lower to secure the position of the whitening strips facing the labial or front surface of the upper front teeth and/or lower front teeth.

The dental appliances 150, 170, 190 and 508 illustrated in FIGS. 13, 14, 15 and 43D, respectively, may be placed into a mouth with crowded teeth or potentially crowded teeth. In an embodiment, a larger-sized dental appliance 150, 170 or 190 may be used. As a result, additional spacing may occur during and/or after the correction which may correct present or future crowding of the teeth. In an embodiment, a smaller-sized dental appliance may be used to close spaces associated with spaced teeth or potentially spaced teeth in children. An individual dental appliance may be designed in various sizes and may be calibrated as to the size of the teeth and/or graduated as to size intervals. As a result, predictions as to size of the dental appliance required may be made more conveniently.

Figure 23:
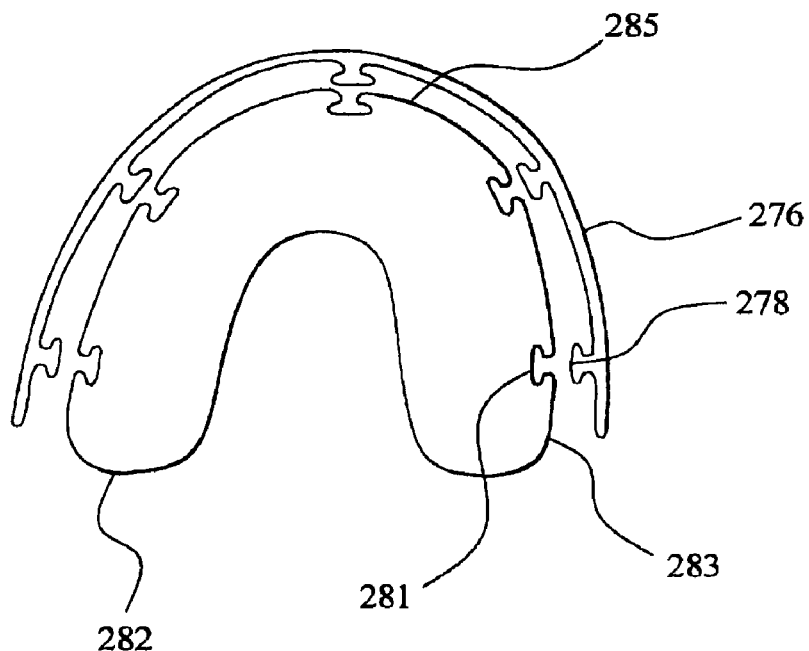
FIG. 23 illustrates a top plan view of a dental appliance in an embodiment of the present invention.
Figure 24:
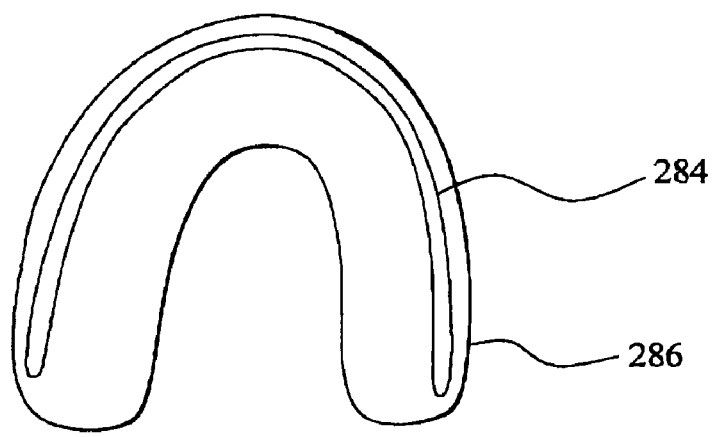
FIG. 24 illustrates a top plan view of a dental appliance in an embodiment of the present invention.

FIG. 23 illustrates a dental appliance 282 which may have a wire 276 which may be snapped onto a buccal surface 283 and/or labial surface 285 of the dental appliance. In an embodiment, ball and socket attachments may be provided on the wire 278 and within an interior (not shown) of the dental appliance 282. The ball and socket attachments may be snapped into an inset 281. In an embodiment, illustrated in FIG. 24, a dental appliance 286 may have a wire 284 molded within the dental appliance 286 within the buccal plastic and/or the lingual plastic of the dental appliance 286. The wire 284 and/or 276 may enable bending of the dental appliance 282, 286 to widen or constrict a size of the dental appliance 282, 286 and, in turn, widen or constrict the dental arch of the user. In another embodiment, the wire 284 may be positioned within molded tubes 250 shown in FIG. 20.

Figure 25A:
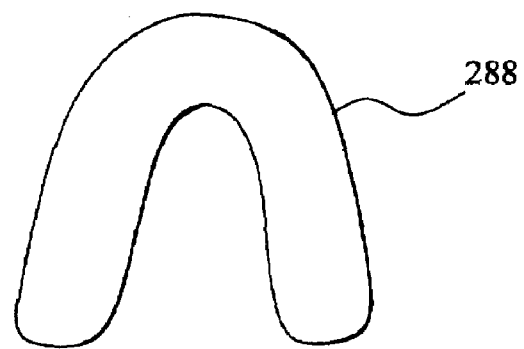
FIG. 25A illustrates a top plan view of a dental appliance in an embodiment of the present invention.
Figure 25B:
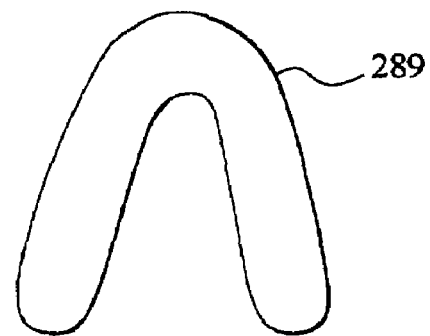
FIG. 25B illustrates a top plan view of a dental appliance in an embodiment of the present invention.
Figure 25C:
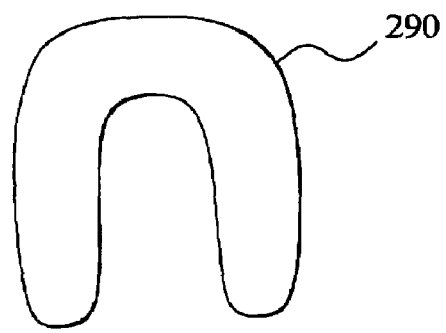
FIG. 25C illustrates a top plan view of a dental appliance in an embodiment of the present invention.

FIGS. 25A through 25C illustrate various shell shapes. Specifically, FIG. 25A illustrates a normal shell shape 288 of a dental appliance. FIG. 25B illustrates a tapered shell shape 289 of a dental appliance. FIG. 25C illustrates a square-type shell shape 290. The shell shapes 288, 289 and 290 may alter the shape of a patient's arch to a normal, tapered, or square arch form, respectively.

Figure 26A:
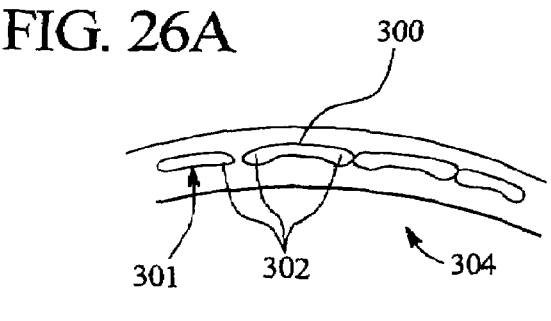
FIG. 26A illustrates a partial top plan view of a dental appliance in an embodiment of the present invention.
Figure 26B:
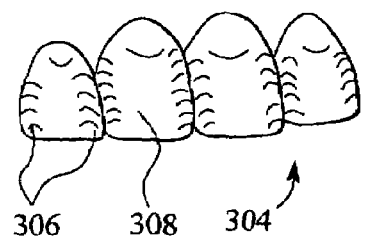
FIG. 26B illustrates a partial front plan view of a dental appliance in an embodiment of the present invention.
Figure 27A:
FIG. 27A illustrates an example of negroid teeth.
Figure 27B:
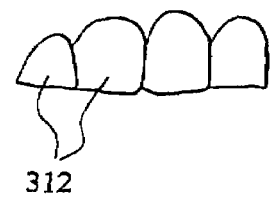
FIG. 27B illustrates an example of Asian and/or Caucasian teeth.

FIGS. 26A and 26B adjustments provided in dental appliances for anatomic features of incisors for racial characteristics. For example, FIG. 26A illustrates upper incisors which may be altered on a lingual surface 301 mesially and distally vertically along marginal ridges of the four upper incisors for Asian users. An inset 302 may be provided into the lingual of the sockets 301 to accommodate a ridge 306 on the lingual surface 301 of the upper incisors 308, as illustrated in FIG. 26B. An example of negroid teeth 310 is illustrated in FIG. 27A. The negroid teeth 310 are more square than either Asian or Caucasian teeth 312, as illustrated in FIG. 27B.

Figure 28:
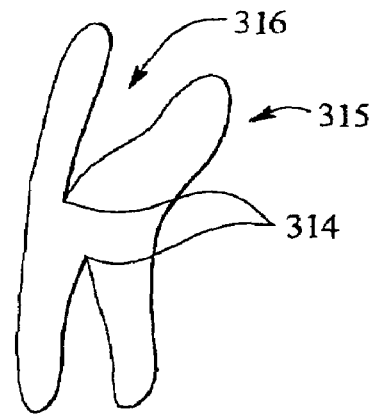
FIG. 28 illustrates a cross-sectional view of a dental appliance in an embodiment of the present invention taken generally along the line E-E.

FIG. 28 illustrates a cross-section 315 of a dental appliance 325. Incisal edges 314 of the incisal sockets 316 and/or canine sockets 329 of the dental appliance 315 may be narrowed and thinned to, for example, a knife-edge thickness 314. As a result, the incisors of the user may be properly squeezed into the socket and/or slot 316 of the dental appliance 315, independent of a thickness labio-lingually of the incisors. The dental appliance 315 may increase corrections of rotation and may aid in the correction of overbite.

Figure 29A:
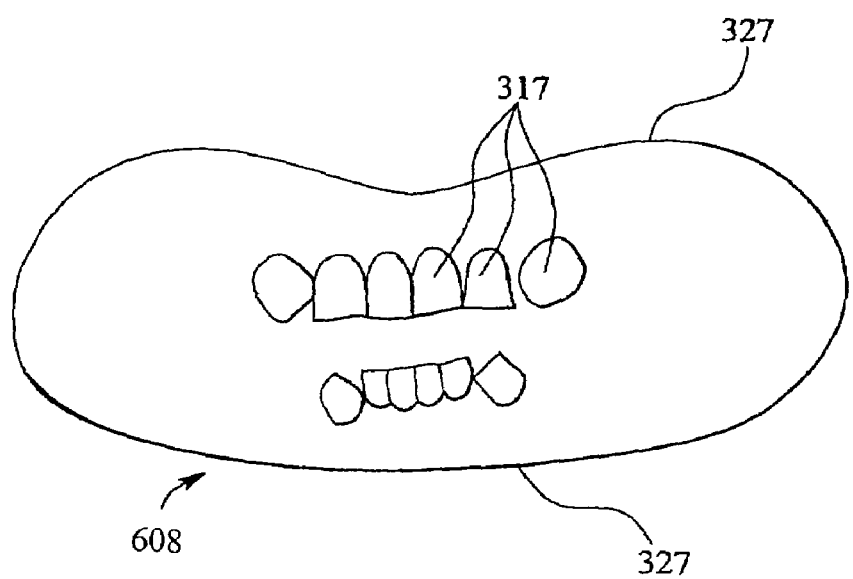
FIG. 29A illustrates a front plan view of a dental appliance in an embodiment of the present invention.
Figure 29B:
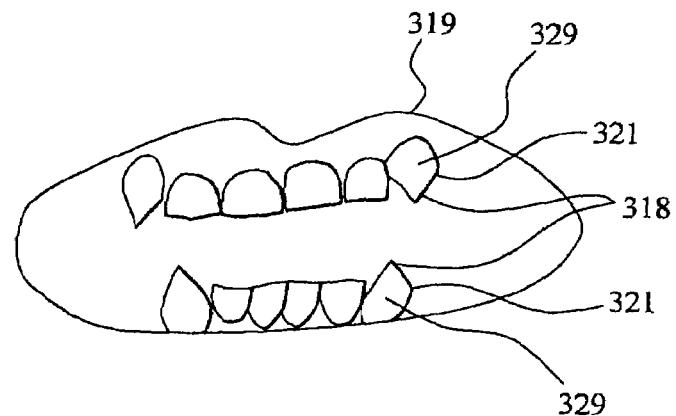
FIG. 29B illustrates a front plan view of a dental appliance in an embodiment of the present invention.
Figure 29C:
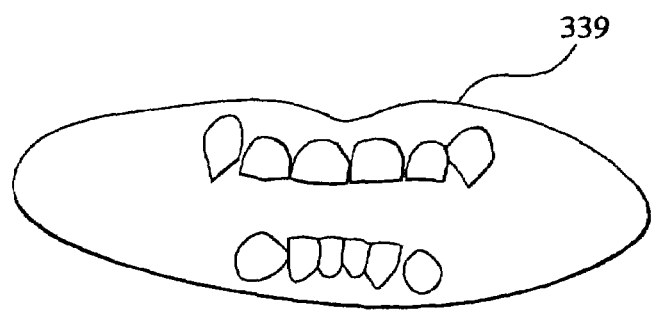
FIG. 29C illustrates a front plan view of a dental appliance in an embodiment of the present invention.

FIG. 29A illustrates a front section 329 of a U-shaped dental appliance 150, 170, 190, and 508 FIGS. 13, 14, 15 and 43D having an occlusal surface (not shown) with individual sockets 317 or slots for more than one tooth(not shown) and where the margins 327 may cover more of the gingival tissue than demonstrated in known dental appliances. FIG. 29C illustrates a dental appliance which has margins 339 which cover a small portion of the gingival tissue. In another embodiment, illustrated in FIG. 29B, canine sockets 329 within the dental appliance 319 may be shaped wherein the canine cuspal area 329 comes to a sharp point 318. In an embodiment, the dental appliance 319 may have an accentuated distal incisal edge 321 of the upper and/or lower canines to enhance mesial space closure towards the midline.

Figure 30:
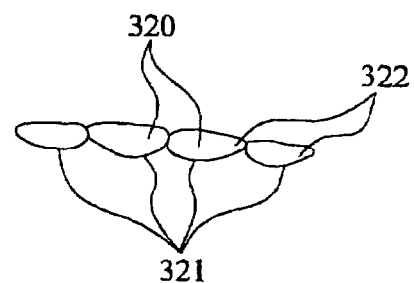
FIG. 30 illustrates a partial top plan view of a dental appliance in an embodiment of the present invention.

FIG. 30 illustrates a top plan view of upper front teeth (not shown) 317 and/or lower front teeth (not shown) wherein sockets 321 may be narrower on a distal side 322 than on a mesial side 320 to encourage the teeth to be moved toward the midline. A mesial side of each tooth may be wider labio-lingually 320 than a labio-lingual dimension on the distal side 322 to move teeth toward the center of the mouth.

Figure 31:
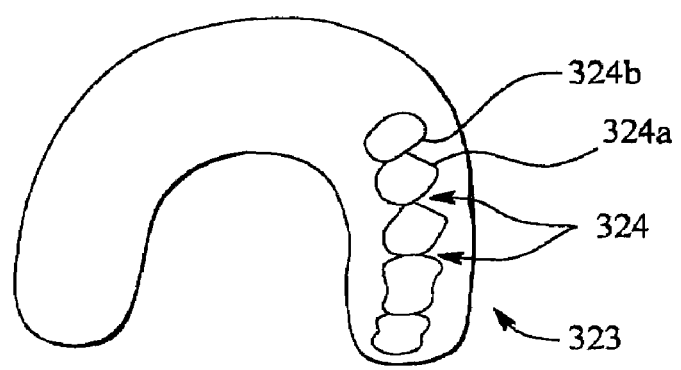
FIG. 31 illustrates a top plan view of a dental appliance in an embodiment of the present invention.

FIG. 31 illustrates a dental appliance 323 which may have interproximal ribs 324 at a mesial location 324a and a distal location 324b of each tooth. The interproximal ribs may assist in guiding teeth into place and may correct rotations, crowding and spacing.

Figure 32:
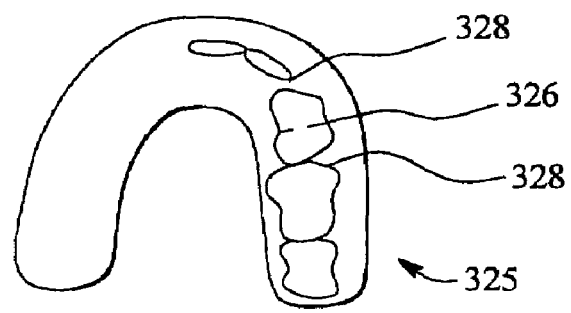
FIG. 32 illustrates a top plan view of a dental appliance in an embodiment of the present invention.

A dental appliance 325 is illustrated in FIG. 32. Interproximal ribs at an extraction site 326 of the dental appliance 325 may be removed to enhance space closure at the site 326 of the extracted tooth. Space closure may also be enhanced at the extraction site 326 by having accentuated ribs 328 on either side of the extraction site 326 with accentuated interproximal ribs. In an embodiment, the increased ribs 328 for teeth on either side of the extraction site 326 may be accentuated to enhance space closure.

Figure 33:
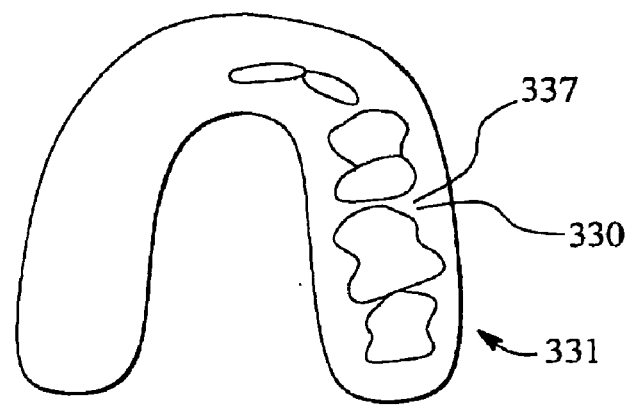
FIG. 33 illustrates a top plan view of a dental appliance in an embodiment of the present invention.

FIG. 33 illustrates a dental appliance 331 which may treat users having upper premolar extractions. An upper first molar area 330 may receive an upper first molar and may rotate the molar in a counter-clockwise direction. As a result, a mesio-buccal cusp may be rotated mesially to more effectively close an extraction site 337.

Figure 34:
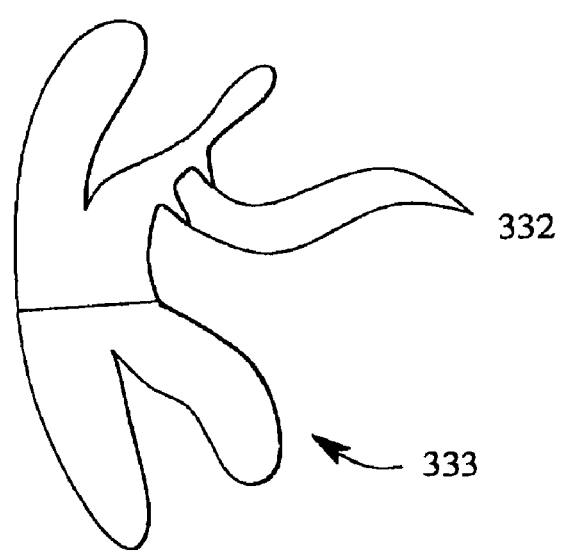
FIG. 34 illustrates a cross-sectional view of a dental appliance in an embodiment of the present invention taken generally along the line E-E.

A cross-section of a dental appliance 333 is illustrated in FIG. 34. Projections 332 may descend downward or inferiorly from a palate behind (lingual to) the incisors of the user. These projections may prevent the tongue of the user from coming forward during swallowing and may correct anterior tongue thrust and anterior open bites and/or finger or thumb sucking.

Figure 35:
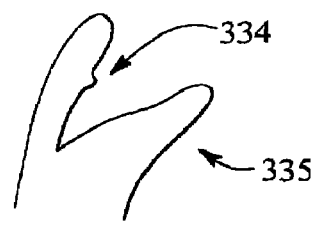
FIG. 35 illustrates a cross-sectional view of a dental appliance in an embodiment of the present invention taken generally along the line E-E.

FIG. 35 illustrates a cross-section of a dental appliance 335 which may have an accentuated horizontal labial rib 334 at a gingival margin of one or more front upper and/or lower teeth 317. The labial rib 334 may increase lingual movement of a root of an upper and/or lower front tooth, and/or increase lingual root torque of upper and/or lower front teeth.

Figure 36:
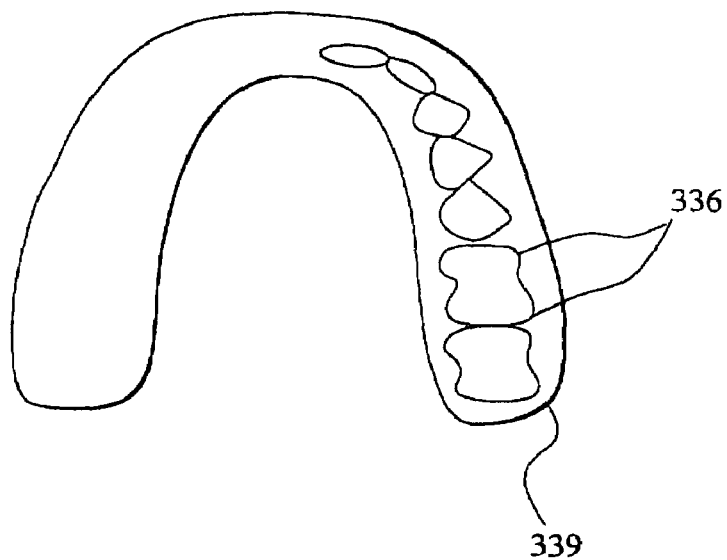
FIG. 36 illustrates a top plan view of a dental appliance in an embodiment of the present invention.

A dental appliance 339 is illustrated in FIG. 36. The dental appliance 339 may have molar sockets 336 which may be squared in shape to receive any type of molar-shaped tooth and may help in correction of overbite and open-bite.

Figure 37:
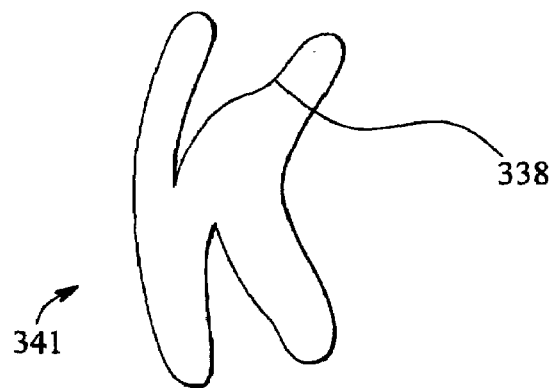
FIG. 37 illustrates a cross-sectional view of a dental appliance in an embodiment of the present invention taken generally along the line E-E.

FIG. 37 illustrates a cross-section of a dental appliance 341 which may have an accentuated cingulum area 338 for an upper front tooth. As a result, the dental appliance 341 may receive all variations in shape and/or size which may be common in the area 338 for an upper front tooth.

In an embodiment, any of the dental appliances illustrated in FIGS. 13, 14, 15 and 43D may have material added to the interior of the dental appliance. The material may be, for example, vinyl, acrylic, silicone or the like. The additional material may serve as a reliner to an interior of the dental appliance and may stabilize movement of the teeth (not shown). The additional material may also increase retention in various areas of the mouth of the user.

Figure 39:
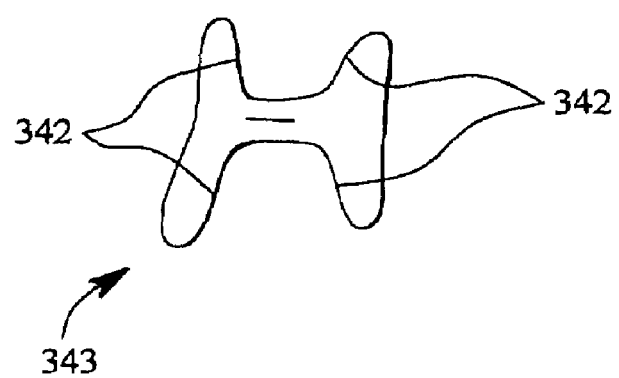
FIG. 39 illustrates a cross-sectional view of a dental appliance in an embodiment of the present invention taken generally along the line C-C.

In an embodiment, a clearance for the soft tissue may be varied on a slant 342 of a dental appliance 343, as illustrated in FIG. 39 generally taken along the line C-C. The increased slant 342 may avoid pushing against soft tissue of the user. Moreover, the slant 342 may be helpful to user of younger ages as well as a stage at which adult teeth are not erupted through tissue which is from the line C-C. This may prevent the margins 43 and/or 45 of the dental appliance 343 from digging into the soft tissue on users of a younger age and/or at any age.

Figure 40A:
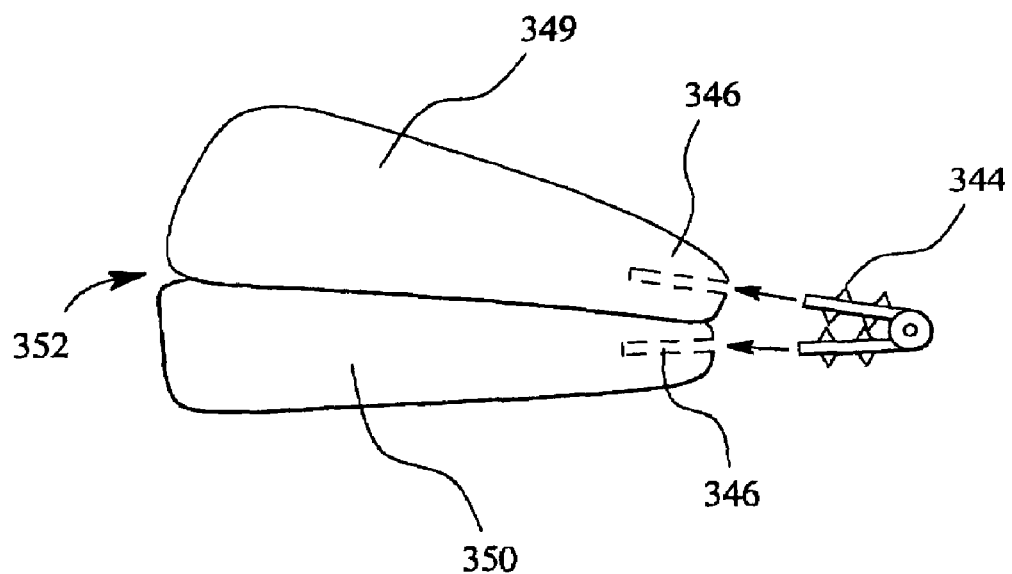
FIG. 40A illustrates a side view of a dental appliance in an embodiment of the present invention.
Figure 40B:
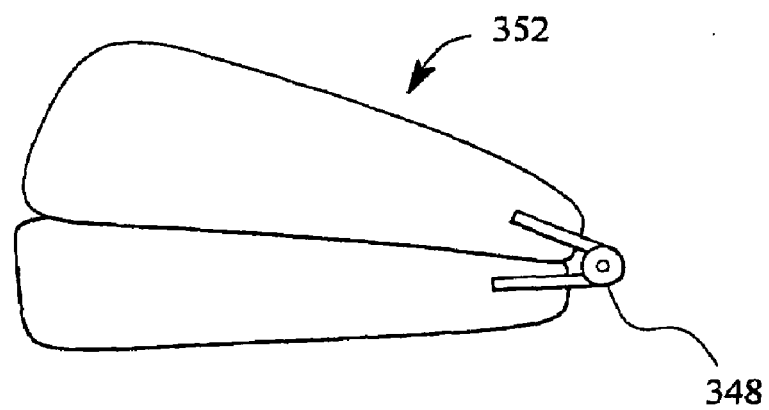
FIG. 40B illustrates a side view of the dental appliance in FIG. 40A.

In an embodiment, illustrated in FIG. 40A, a dental appliance 352 may have a detachable upper shell 349 and a lower shell 350. In an embodiment, a hinge 344 may attach the upper shell 349 to the lower shell 350 and may be constructed from, for example, metal, plastic or other material. The hinge 344 may be attached to the upper shell 349 and the lower shell 350 at slots 346 at a rear end 348 of the dental appliance 352. FIG. 40B illustrates the dental appliance 352 wherein the hinge 344 is attached to the upper shell 349 and the lower shell 350.

In an embodiment, a gingival coverage of the labial buccal and lingual shields may be lowered to cover only crowns of the teeth as illustrated in FIG. 29C. FIG. 29C illustrates the labial shield which may be lowered in the front area while FIG. 29A illustrates the labial shield elevated to cover a substantial portion of the gingival tissue.

In an embodiment, the teeth of the user may be straightened prior to adult collagenous fiber formation. Moreover, after the teeth are properly guided, fibers may form to stabilize a correction of the teeth (not shown).

In another embodiment, a dental appliance may straighten the teeth sufficiently to avoid or reduce regular orthodontic treatment, such as, for example, the use of braces at a later stage of treatment (not shown).

In an embodiment, a dental appliance may correct jaw relations, such as, for example, a Class I, II and/or III jaw relation. The dental appliance may advance the mandible and may encourage the mandible to grow into a correct position. Further, the dental appliance may restrict the upper jaw from developing forward (not shown) and may allow the side teeth to erupt into a perfect intercuspation, such as that illustrated in FIG. 41A.

In an embodiment, a dental appliance may have interproximal ribs wherein the interproximal ribs are removed in certain areas to allow the teeth to slip or shift mesio-distally into a proper occlusion (not shown).

In another embodiment, a dental appliance may be constructed having various hardnesses and/or resiliencies of material (not shown). In an embodiment, the dental appliance may have a combination of hardness and resiliency in any area of the dental appliance. Moreover, the dental appliance may be transparent. In another embodiment the dental appliance(s) may be molded in different colors, which may increase the wear of the appliance by the user.

In an embodiment, a dental appliance may have sockets or slots for more than one tooth. The dental appliance may treat any number of deciduous, permanent, missing, or erupting teeth. In addition, the dental appliance may treat teeth at various levels or positions during any time of exfoliation, eruption, chronological or dental or skeletal age of the user.

In another embodiment, a larger dental appliance may be placed in the mouth of the user having a smaller-sized mouth and/or crowded teeth or in anticipation of crowding at ages less than seven years of age. In another embodiment, a dental appliance may be placed in the mouth of the user having larger adult teeth wherein the adult teeth may erupt to replace smaller deciduous teeth. Moreover, a larger-sized dental appliance may be placed in the mouth of a user having larger teeth to properly straighten the teeth.

Figure 42A:
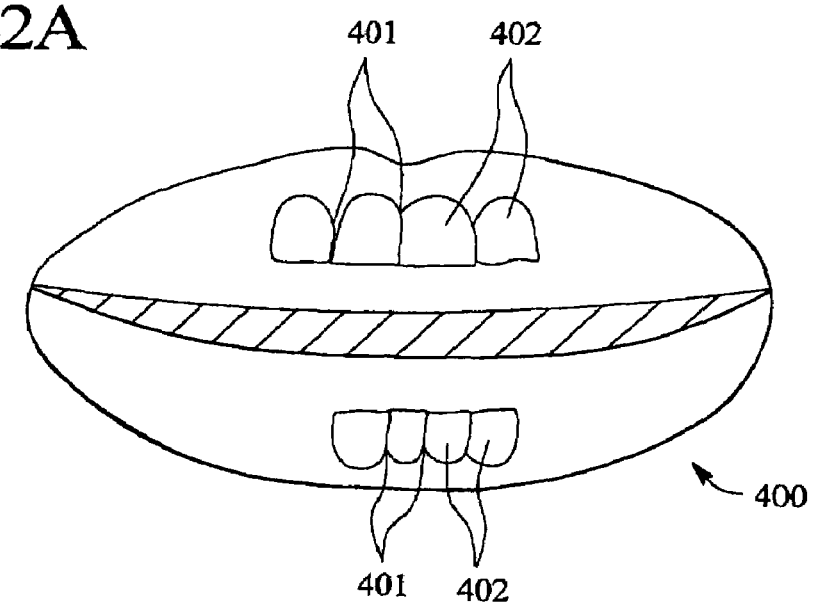
FIG. 42A illustrates a front plan view of a dental appliance in an embodiment of the present invention.
Figure 42B:
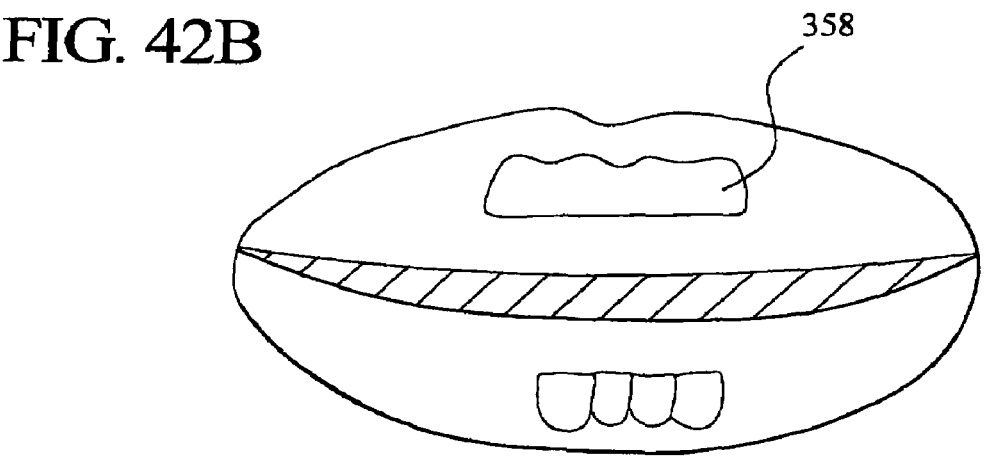
FIG. 42B illustrates a front plan view of the dental appliance in FIG. 42A in an embodiment of the present invention.

FIG. 42A illustrates a dental appliance 400 having interproximal ribs 401 and/or individual sockets 402 for certain teeth, such as, for example, the upper and/or lower incisors. FIG. 42B illustrates the dental appliance 400 in an embodiment wherein individual slots for teeth may be removed, leaving a single slot 358 for receiving teeth. The removal of ribs in between any or all teeth in the dental appliance of FIGS. 13, 14, 15 and 43D may allow teeth to shift or move mesio-distally to adjust the intercuspation or occlusion.

In an embodiment, a dental appliance may be molded in a water-absorbent plastic or other material (not shown). In another embodiment, the dental appliance may be molded in part of a non-absorbent material in combination with an absorbent material to absorb saliva and/or change color in relation to an amount of time the dental appliance is kept in the mouth depending on a percentage of each material being present in the dental appliance. The dental appliance may also be constructed from a non-absorbent material wherein the dental appliance does not change color. A dental appliance that may be absorbent may absorb, for example, fluoride. The fluoride may leach out during use of the dental appliance and may prevent tooth decay (not shown).

All embodiments applied to various appliances including those of FIGS. 13, 14., 15 and 43D may or may not be made in one or more sizes depending on the sizes and/or shapes of the teeth of users. All may be dispensed by an automated dispenser with or without a manual or computerized automated diagnosis, with digitalized photos, x-rays or the like.

It should be understood that various changes and modifications to the presently preferred embodiments described herein will be apparent to those skilled in the art. Such changes and modifications may be made without departing from the spirit and scope of the present invention and without diminishing its attendant advantages.

I claim:

1. A dental appliance designed to be worn in a mouth of a user wherein the user has one or more types of teeth wherein one of the types of teeth is molars wherein a last molar is located furthest rearward into the mouth of the user, the dental appliance comprising:

a generally U-shaped base having a top portion and a bottom portion wherein the generally U-shaped base has an occlusal surface wherein the occlusal surface contacts the teeth when the base is worn wherein the base has a thickness defined between a first end and a second end wherein the occlusal surface contacts each of the molars of the user when the base is worn to prevent the molar from achieving a malocclusion position wherein a socket is formed in the generally U-shaped base wherein the last molar is inserted into the socket and further wherein the first end and the second end extend beyond the last molar to a point further rearward into the mouth of the user than the last molar; and a hinge connecting the top portion to the bottom portion wherein the hinge has an upper plate that inserts into a top aperture in the top portion wherein the hinge has a lower plate that inserts into a bottom aperture in the bottom portion wherein the hinge may be removed and re-inserted into the upper aperture and the lower aperture to reversibly detach and re-attach the top portion to the bottom portion.

2. The dental appliance of claim 1 wherein the hinge enables the base to be folded.

3. The dental appliance of claim 1 wherein the base is transparent.

4. The dental appliance of claim 1 wherein the occlusal surface is flat.

5. The dental appliance of claim 1 wherein the hinge prevents movement between the top portion and the bottom portion.

6. The dental appliance of claim 1 further comprising:
   a wire imbedded within the base wherein the wire extends from the first end of the base to the second end of the base.

7. The dental appliance of claim 1 wherein the base is constructed from a first material and a second material wherein the first material has a lesser degree of rigidity than the second material.

8. A dental appliance designed to be worn in a mouth of a user wherein the user has an upper arch having upper teeth and a lower arch having lower teeth wherein one of the upper teeth and the lower teeth are molars, the dental appliance comprising:

a generally U-shaped upper base which contacts upper teeth of the user when the upper base is worn;

a generally U-shaped lower base adjacent to the upper base wherein the lower base contacts lower teeth of the user when the lower base is worn wherein the upper base and the lower base are made from a first material; and a hinge connecting the upper base and the lower base wherein the hinge is sized to insert into slots in the upper base and the lower base wherein a front section of the upper base separates from a front section of the lower base via the hinge wherein the hinge may be reversibly removed from the slots to allow the upper base to separate in its entirety from the lower base wherein the hinge is made from a second material wherein the second material is harder than the first material.

9. The dental appliance of claim 8 further comprising:

holes within the base wherein the user breathes through the holes.

10. The dental appliance of claim 8 further comprising:
lingual tabs extending horizontally from the lower base wherein the lingual tabs extend rearward into the mouth.

11. The dental appliance of claim 8 further comprising:
one or more sockets within the upper base wherein the sockets are sized to fit at least two or more teeth of the user.

12. The dental appliance of claim 8 further comprising:
ribs formed within the upper base at projection points on the upper base wherein the ribs project from the upper base toward the teeth wherein an end portion of the rib farthest from the projection point contacts the teeth to guide the teeth into a correct position.

13. The dental appliance of claim 8 wherein the upper base is constructed from a moisture-absorbent material.

14. A dental appliance designed to be worn in a mouth of a user wherein the user has a tongue, an upper arch having upper teeth and a lower arch having lower teeth, the dental appliance comprising:
a generally U-shaped upper base which contacts upper teeth of the user when the upper base is worn wherein a concaved portion is formed on the upper base wherein the concave portion is a depression in the upper base wherein the concave portion is shaped like the tongue and moves the tongue of the user outward with respect to the lower arch of the user wherein the upper base widens the upper arch of the user wherein the upper base has an exterior surface;
a generally U-shaped lower base adjacent to the upper base wherein the lower base contacts lower teeth of the user when the lower base is worn wherein the lower base has an exterior surface; and
a hinge attaching the upper base to the lower base wherein an upper hinge plate inserts into a first slot and a lower hinge plate inserts into a second slot wherein the first slot is in the upper base and the second slot is in the lower base wherein a pivot connects the upper plate to the lower plate and resides outside of the exterior surface of the upper base and the exterior surface of the lower base wherein the hinge is removed and re-inserted into the first slot and the second slot to reversibly detach and re-attach the upper base to the lower base wherein the upper base, the lower base and the hinge are designed by stereolithography.

15. The dental appliance of claim 14 further comprising:
a socket within the upper base shaped to correspond to a shape of one of the teeth.

16. The dental appliance of claim 14 further comprising:
a socket within the lower base shaped to correspond to a shape of one of the teeth.

17. The dental appliance of claim 14 further comprising:
a socket within the upper base wherein the socket is flat.

18. The dental appliance of claim 14 further comprising:
a socket within the lower base wherein the socket is flat.

19. The dental appliance of claim 14 further comprising:
lingual tabs extending horizontally from the lower base wherein the lingual tabs extend rearward.

20. The dental appliance of claim 14 further comprising:
holes within the upper base.

21. The dental appliance of claim 14 further comprising:
holes within the lower base.

22. The dental appliance of claim 14 further comprising:
a labial shield extending vertically from the upper base wherein the labial shield covers the upper teeth and lower teeth.

23. A dental appliance designed to be worn in a mouth of a user wherein the user has upper teeth, lower teeth and a tongue, the dental appliance comprising:
a generally U-shaped upper base having a flat occlusal surface;
a generally U-shaped lower base having a flat occlusal surface; and
a hinge attaching the upper base to the lower base wherein the upper base and the lower base are sized to fit users of various types of dentitions wherein the hinge has an upper portion and a lower portion wherein the upper base has a first slot and a second slot wherein the upper portion of the hinge is removed and re-inserted into the first slot and lower portion of the hinge is removed and re-inserted into the second slot to reversibly detach and re-attach the upper base to the lower base.

24. The dental appliance of claim 23 wherein the hinge has a pivot that connects the upper portion of the hinge to the lower portion of the hinge wherein the pivot resides outside of the upper base and the lower base.

25. The dental appliance of claim 23 wherein the hinge is more rigid than the upper base and the lower base.

26. The dental appliance of claim 23 further comprising:
holes within the upper base.

27. The dental appliance of claim 23 further comprising:
holes within the lower base.

28. The dental appliance of claim 23 further comprising:
a labial shield extending vertically from the upper base past the upper teeth of a user.

29. The dental appliance of claim 23 further comprising:
a cavity formed within the lower base wherein the cavity is shaped like the tongue of the user and the cavity moves the tongue outward with respect to the mouth of the user.

30. The dental appliance of claim 23 further comprising:
a cavity formed within the upper base wherein the cavity is shaped like the tongue of the user and the cavity moves the tongue to an elevated position with respect to the lower teeth of the user.

31. The dental appliance of claim 23 further comprising:
a cavity formed within the upper base and the lower base wherein the cavity is shaped like the tongue of the user and the cavity moves the tongue to an elevated position with respect to the lower teeth of the user.

32. A dental appliance designed to be worn in a mouth of a user wherein the user has a tongue, an upper arch having upper teeth and a lower arch having lower teeth, the dental appliance comprising:
a generally U-shaped upper base which contacts upper teeth of the user when the upper base is worn wherein the upper base has at least one female portion formed at a posterior end of the upper base;
a generally U-shaped lower base adjacent to the upper base wherein the lower base contacts lower teeth of the user when the lower base is worn wherein the lower base has at least one female portion formed at a posterior end of the lower base wherein the lower base has a lingual surface wherein a spike is formed on the lingual surface of the lower base wherein the spike contacts the tongue of the user; and
a hinge having a first end which is inserted into a cavity within the upper base and a second end which is inserted into a cavity within the lower base wherein removing the hinge from the cavity within the upper base and removing the hinge from the cavity within the lower base separates the upper base from the lower base wherein returning the hinge to the cavity within the upper base and returning the hinge to the cavity within the lower base re-attaches the upper base to the lower base.

33. The dental appliance of claim 32 wherein the hinge is constructed from metal.

34. The dental appliance of claim 32 wherein the upper base and the lower base are designed by stereolithography.

35. The dental appliance of claim 32 wherein the upper base and the lower base are constructed manually.

36. The dental appliance of claim 32 further comprising:
a socket within the upper base wherein the socket is shaped to correspond to a shape of at least one of the teeth of the user.

37. The dental appliance of claim 32 further comprising:
a socket within the lower base wherein the socket is shaped to correspond to a shape of at least one of the teeth of the user.

38. The dental appliance of claim 32 wherein the hinge is more rigid than the upper base and the lower base.

39. The dental appliance of claim 32 further comprising:
lingual tabs extending horizontally from the lower base into the mouth.

40. The dental appliance of claim 32 further comprising:
a labial shield extending vertically from the upper base past the upper teeth of the user.

41. A dental appliance designed to be worn in a mouth of a user having an upper arch having upper teeth and a lower arch having lower teeth, the dental appliance comprising:
a generally U-shaped upper base which contacts the upper teeth of the user when the upper base is worn wherein the upper base has a first arch width defined between a first end of the upper base and a second end of the upper base;
a generally U-shaped lower base adjacent to the upper base wherein the lower base contacts lower teeth of the user when the lower base is worn wherein the lower base has a second arch width defined between a first end of the lower base and the second end of the lower base wherein the second arch width of the lower base is greater than or is less than the first arch width of the upper base;
a slot within the lower base or the upper base wherein the slot is sized to receive one or more teeth of the user; and
a hinge connecting the upper base and the lower base wherein the hinge may be removed from and reconnected to the upper base and the lower base to reversibly detach and reattach the upper base to the lower base.

42. The dental appliance of claim 41 wherein the slot is preformed to receive one or more teeth of the user.

43. The dental appliance of claim 41 wherein the slot is customized to receive one or more teeth of the user.

44. The dental appliance of claim 41 further comprising:
a socket within the lower base or the upper base wherein the socket is preformed to receive one or more teeth of the user.

45. The dental appliance of claim 41 further comprising:
a socket within the lower base or the upper base wherein the socket is customized to receive one or more teeth of the user.

46. The dental appliance of claim 41 further comprising:
holes within the lower base or the upper base wherein the user breathes through the holes.

47. The dental appliance of claim 41 further comprising:
lingual tabs extending from the lower base wherein the lingual tabs extend rearward into the mouth.

48. The dental appliance of claim 41 further comprising:
ribs formed within the upper base wherein the ribs guide the teeth into a correct position.

49. The dental appliance of claim 41 wherein the upper base is constructed from a moisture-absorbent material.

50. A dental appliance designed to be worn in a mouth of a user having an upper arch having upper teeth and a lower arch having lower teeth, the dental appliance comprising:
a generally U-shaped upper base which contacts the upper teeth of the user when the upper base is worn;
a generally U-shaped lower base adjacent to the upper base wherein the lower base contacts lower teeth of the user when the lower base is worn;
an attachment within the lower base or the upper base; and
a hinge having a length defined between a first end and a second end wherein the hinge connects the upper base and the lower base wherein the first end of the hinge inserts into the upper base and farther wherein the second end of the hinge inserts into the lower base wherein the hinge may be removed and re-inserted into the upper base and the lower base to reversibly detach and re-attach the upper base to the lower base.

51. The dental appliance of claim 50 further comprising:
a socket within the lower base or the upper base wherein the socket is sized to receive one or more teeth of the user.

52. The dental appliance of claim 50 further comprising:
a socket within the lower base or the upper base wherein the socket is sized to receive one or more teeth of the user.

53. The dental appliance of claim 50 further comprising:
lingual tabs extending horizontally from the lower base or the upper base wherein the lingual tabs extend rearward into the mouth.

54. The dental appliance of claim 50 further comprising:
ribs formed within the upper base or the lower base wherein the ribs project from the upper base or the lower base wherein an end portion of the rib contacts the teeth and guides the teeth into a correct position.

55. The dental appliance of claim 50 wherein the attachment is a hook attached to another device worn by the user.

56. The dental appliance of claim 50 wherein the attachment is a tube connected to a wire.

57. The dental appliance of claim 50 wherein the attachment is a clasp that extends around a mesial side of a tooth and a distal side of the tooth.

58. The dental appliance of claim 50 further comprising:
elastics or a head gear attached to the attachment.

59. The dental appliance of claim 50 wherein the attachment secures the lower base or the upper base to the mouth of the user.

60. The dental appliance of claim 50 wherein the attachment is constructed from metal or plastic.

61. A dental appliance designed to be worn by a user wherein the user has an upper arch having upper teeth and a lower arch having lower teeth wherein at least one of the teeth is a molar and another tooth is a last molar that is located furthest rearward into the mouth of the user, the dental appliance comprising:
a generally U-shaped lower base wherein the lower base contacts the lower teeth of the user when the lower base is worn;
a generally U-shaped upper base wherein the upper base contacts the upper teeth of the user when the upper base is worn wherein the upper base has a lingual surface extending outwardly with respect to the upper arch of the user wherein the lingual surface has a projection or a rib formed wherein the projection or the rib extends inwardly with respect to the lower arch of the user wherein the projection or the rib blocks a space between the upper arch and the lower arch to correct thumb sucking of the patient; and
a hinge having a first end reversibly inserted into a first cavity and a second end reversibly inserted into a second cavity wherein the first cavity is within the upper base and the second cavity is within the lower base.

62. The dental appliance of claim 61 wherein the projection or the rib is positioned on the lingual surface so as to be adjacent to an incisor when the base is worn.

63. The dental appliance of claim 61 wherein the lingual surface is flat in an area surrounding the projection or the rib.

64. The dental appliance of claim 61 further comprising:
a lingual tab extending horizontally rearward from the base.

65. The dental appliance of claim 61 further comprising:
a wire embedded within the base wherein the base has a first end and a second end wherein the first end and the second end extend beyond the last molar to a point further rearward into the mouth of the user than the last molar and the wire extends from the first end to the second end.

66. The dental appliance of claim 61 wherein the base is constructed from a moisture-absorbent material.

67. The dental appliance of claim 61 further comprising:
a socket within the base wherein the socket is sized to receive one or more teeth of the user.

68. The dental appliance of claim 41 further comprising:
ribs formed within the lower base wherein the ribs project from the lower base toward the teeth wherein an end portion of the rib contacts the teeth to guide the teeth into a correct position.

69. The dental appliance of claim 41 wherein the lower base is constructed from a moisture-absorbent material.

70. A dental appliance designed to be worn in a mouth of a user having an upper arch having upper teeth and a lower arch having lower teeth, the dental appliance comprising:
a generally U-shaped upper base which contacts the upper teeth of the user when the upper base is worn;
a generally U-shaped lower base adjacent to the upper base wherein the lower base contacts lower teeth of the user when the lower base is worn;
a cavity formed within the upper base or the lower base wherein the cavity is a depression in the upper base or the lower base shaped and sized to receive a tongue of the user wherein the cavity moves the tongue outwardly with respect to the lower base; and
a hinge connecting the upper base and the lower base and removably attached to the upper base and the lower base so that removing the hinge from an upper slot in the upper base and a lower slot in the lower base allows the upper base to separate in its entirety from the lower base and returning the hinge to the upper slot in the upper base and the lower slot in the lower base re-attaches the upper base to the lower base.

71. The dental appliance of claim 70 further comprising:
a socket within the lower base or the upper base wherein the socket is sized to receive one or more teeth of the user.

72. The dental appliance of claim 70 further comprising:
a socket within the lower base or the upper base wherein the socket is sized to receive one or more teeth of the user.

73. The dental appliance of claim 70 further comprising:
lingual tabs extending horizontally from the lower base or the upper base wherein the lingual tabs extend rearward into the mouth.

74. The dental appliance of claim 70 further comprising:
ribs formed within the upper base or the lower base wherein the ribs guide the teeth into a correct position.

75. A dental appliance designed to be worn in a mouth of a user having upper teeth and lower teeth wherein the upper teeth and the lower teeth are comprised of one or more types of teeth wherein one of the types of teeth is molars wherein the molars are located furthest rearward into the mouth of the user, the dental appliance comprising:
a generally U-shaped upper base having an upper occlusal surface wherein the upper occlusal surface contacts the upper teeth and guides the upper teeth into a correct position;
a generally U-shaped lower base connected to the upper base wherein the lower base has a lower occlusal surface wherein the lower occlusal surface contacts the lower teeth and guides the lower teeth into a correct position and wherein the upper occlusal surface and the lower occlusal surface are adjacent and have a combined thickness wherein the upper occlusal surface contacts each molar of the user when the upper base and the lower base are worn to prevent the molar from achieving a malocclusion position; and
sockets within the upper base wherein the sockets are square in shape.

76. A dental appliance designed to be worn in a mouth of a user having upper teeth and lower teeth wherein the upper teeth and the lower teeth are comprised of one or more types of teeth wherein one of the types of teeth is molars wherein the molars are located furthest rearward into the mouth of the user, the dental appliance comprising:
a generally U-shaped upper base having an upper occlusal surface wherein the upper occlusal surface contacts the upper teeth and guides the upper teeth into a correct position;
a generally U-shaped lower base connected to the upper base wherein the lower base has a lower occlusal surface wherein the lower occlusal surface contacts the lower teeth and guides the lower teeth into a correct position and wherein the upper occlusal surface and the lower occlusal surface are adjacent and have a combined thickness wherein the upper occlusal surface contacts each molar of the user when the upper base and the lower base are worn to prevent the molar from achieving a malocclusion position wherein the upper base is wider than the lower base; and
connecting means attached to the upper base and the lower base wherein the connecting means may be removed from and re-connected to the upper base and the lower base to reversibly detach and re-attach the upper base to the lower base.

77. A dental appliance designed to be worn in a mouth of a user wherein the user has a tongue, upper teeth and lower teeth wherein the upper teeth and the lower teeth are comprised of one or more types of teeth wherein one of the types of teeth is molars wherein the molars are located furthest rearward into the mouth of the user, the dental appliance comprising:
a generally U-shaped upper base having an upper occlusal surface wherein the upper occlusal surface contacts the upper teeth and guides the upper teeth into a correct position wherein a concaved portion is a depression formed in the upper base wherein the concaved portion is shaped like the tongue and moves the tongue to an elevated position with respect to the lower teeth of the user; and
a generally U-shaped lower base connected to the upper base wherein the lower base has a lower occlusal surface wherein the lower occlusal surface contacts the lower teeth and guides the lower teeth into a correct position and wherein the upper occlusal surface and the lower occlusal surface are adjacent and have a combined thickness wherein the upper occlusal surface contacts each molar of the user when the upper base and the lower base are worn to prevent the molar from achieving a malocclusion position, a hinge connecting the upper base and the lower base wherein the hinge allows the upper base to be pivoted toward the lower base and the hinge may be reversibly removed to allow the upper base to separate in its entirety from the lower base.

78. A dental appliance designed to be worn in a mouth of a user wherein the user has a tongue, upper teeth and lower teeth wherein the upper teeth and the lower teeth are comprised of one or more types of teeth wherein one of the types of teeth is molars wherein the molars are located furthest rearward into the mouth of the user, the dental appliance comprising:

a generally U-shaped upper base having an upper occlusal surface wherein the upper occlusal surface contacts the upper teeth and guides the upper teeth into a correct position wherein a concaved portion is a depression formed in the upper base wherein the concaved portion is shaped like the tongue and moves the tongue to an elevated position with respect to the lower teeth of the user;

a generally U-shaped lower base connected to the upper base wherein the lower base has a lower occlusal surface wherein the lower occlusal surface contacts the lower teeth and guides the lower teeth into a correct position and wherein the upper occlusal surface and the lower occlusal surface are adjacent and have a combined thickness wherein the upper occlusal surface contacts each molar of the user when the upper base and the lower base are worn to prevent the molar from achieving a malocclusion position;

a hinge connecting the upper base to the lower base wherein the hinge has an upper plate that inserts into a top aperture in the upper base wherein the hinge has a lower plate that inserts into a bottom aperture in the lower base wherein the hinge may be removed from and re-inserted into the upper aperture and the lower aperture to reversibly detach and re-attach the upper base to the lower base; and sockets within the upper base wherein the sockets are square in shape.

79. A dental appliance designed to be worn in a mouth of a user wherein the user has a tongue, upper teeth and lower teeth wherein the upper teeth and the lower teeth are comprised of one or more types of teeth wherein one of the types of teeth is molars wherein the molars are located furthest rearward into the mouth of the user, the dental appliance comprising:

a generally U-shaped upper base having an upper occlusal surface wherein the upper occlusal surface contacts the upper teeth and guides the upper teeth into a correct position wherein a concaved portion is a depression formed in the upper base wherein the concaved portion is shaped like the tongue and moves the tongue to an elevated position with respect to the lower teeth of the user;

a generally U-shaped lower base connected to the upper base wherein the lower base is wider than the upper base wherein the lower base has a lower occlusal surface wherein the lower occlusal surface contacts the lower teeth and guides the lower teeth into a correct position and wherein the upper occlusal surface and the lower occlusal surface are adjacent and have a combined thickness wherein the upper occlusal surface contacts each molar of the user when the upper base and the lower base are worn to prevent the molar from achieving a malocclusion position; and a hinge connecting the upper base to the lower base wherein the hinge has an upper plate that inserts into a top aperture in the upper base wherein the hinge has a lower plate that inserts into a bottom aperture in the lower base wherein the hinge may be removed from and re-inserted into the upper aperture and the lower aperture to reversibly detach and re-attach the upper base to the lower base.

80. A dental appliance designed to be worn in a mouth of a user wherein the user has a tongue, upper teeth and lower teeth wherein the upper teeth and the lower teeth are comprised of one or more types of teeth wherein one of the types of teeth is molars wherein the molars are located furthest rearward into the mouth of the user, the dental appliance comprising:

a generally U-shaped upper base having an upper occlusal surface wherein the upper occlusal surface contacts the upper teeth and guides the upper teeth into a correct position wherein a concaved portion is a depression formed in the upper base wherein the concaved portion is shaped like the tongue and moves the tongue to an elevated position with respect to the lower teeth of the user;

a generally U-shaped lower base connected to the upper base wherein the upper base is wider than the lower base wherein the lower base has a lower occlusal surface wherein the lower occlusal surface contacts the lower teeth and guides the lower teeth into a correct position and wherein the upper occlusal surface and the lower occlusal surface are adjacent and have a combined thickness wherein the upper occlusal surface contacts each molar of the user when the upper base and the lower base are worn to prevent the molar from achieving a malocclusion position; and a hinge connecting the upper base to the lower base wherein the hinge has an upper plate that inserts into a top aperture in the upper base wherein the hinge has a lower plate that inserts into a bottom aperture in the lower base wherein the hinge may be removed from and re-inserted into the upper aperture and the lower aperture to reversibly detach and re-attach the upper base to the lower base.

* * * * *